(12) United States Patent
Saunders et al.

(10) Patent No.: US 8,318,509 B2
(45) Date of Patent: Nov. 27, 2012

(54) TWO-PHASE OPTICAL ASSAYS FOR ANALYTES OF NO INTRINSIC OPITCAL CONTRAST

(76) Inventors: Paul Alexander Saunders, San Carlos, CA (US); Alex Michael Saunders, San Carlos, CA (US)

( * ) Notice: Subject to any disclaimer, the term of this patent is extended or adjusted under 35 U.S.C. 154(b) by 0 days.

(21) Appl. No.: 13/204,539

(22) Filed: Aug. 5, 2011

(65) Prior Publication Data

US 2012/0034632 A1    Feb. 9, 2012

Related U.S. Application Data

(60) Provisional application No. 61/371,684, filed on Aug. 7, 2010.

(51) Int. Cl.
*G01N 33/543* (2006.01)

(52) U.S. Cl. ...... 436/518; 435/7.92; 435/7.93; 436/501; 436/523

(58) Field of Classification Search .................. None
See application file for complete search history.

(56) References Cited

U.S. PATENT DOCUMENTS

| 4,857,454 | A | 8/1989 | Freundlich et al. |
| 5,674,699 | A | 10/1997 | Saunders et al. |
| 6,294,342 | B1 * | 9/2001 | Rohr et al. ............ 435/7.1 |
| 7,851,229 | B2 | 12/2010 | Saunders |

* cited by examiner

*Primary Examiner* — Gary W Counts
(74) *Attorney, Agent, or Firm* — Hsiu-Ming Saunders; Intellectual Property Connections, Inc.

(57) ABSTRACT

Methods and kits for performing a two-phase optical assay for one or more than one analyte without intrinsic optical contrast in a sample are disclosed. The method requires use of a functionalized microparticle immobilized with two or more than functional components and an additional set of one or more than one functional component. The assay can be performed in one single container and does not need a wash step.

20 Claims, 13 Drawing Sheets

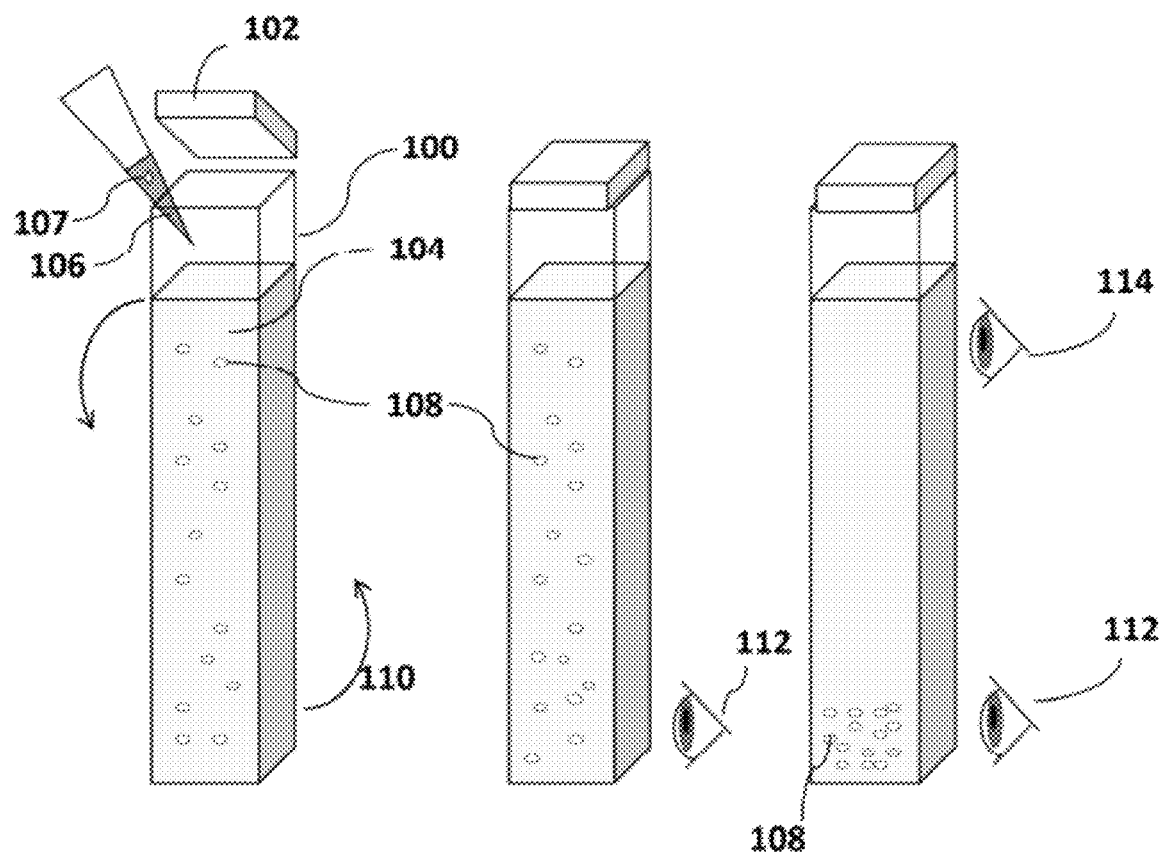
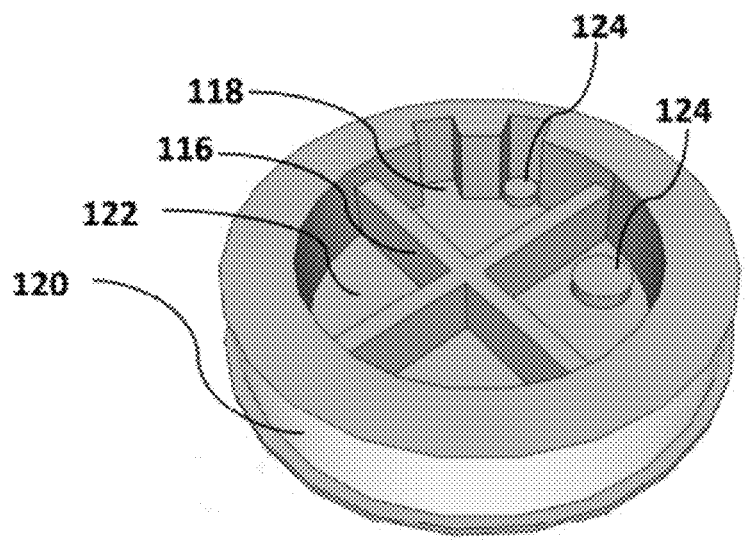
FIG. 1A  FIG. 1B  FIG. 1C
FIG. 1D

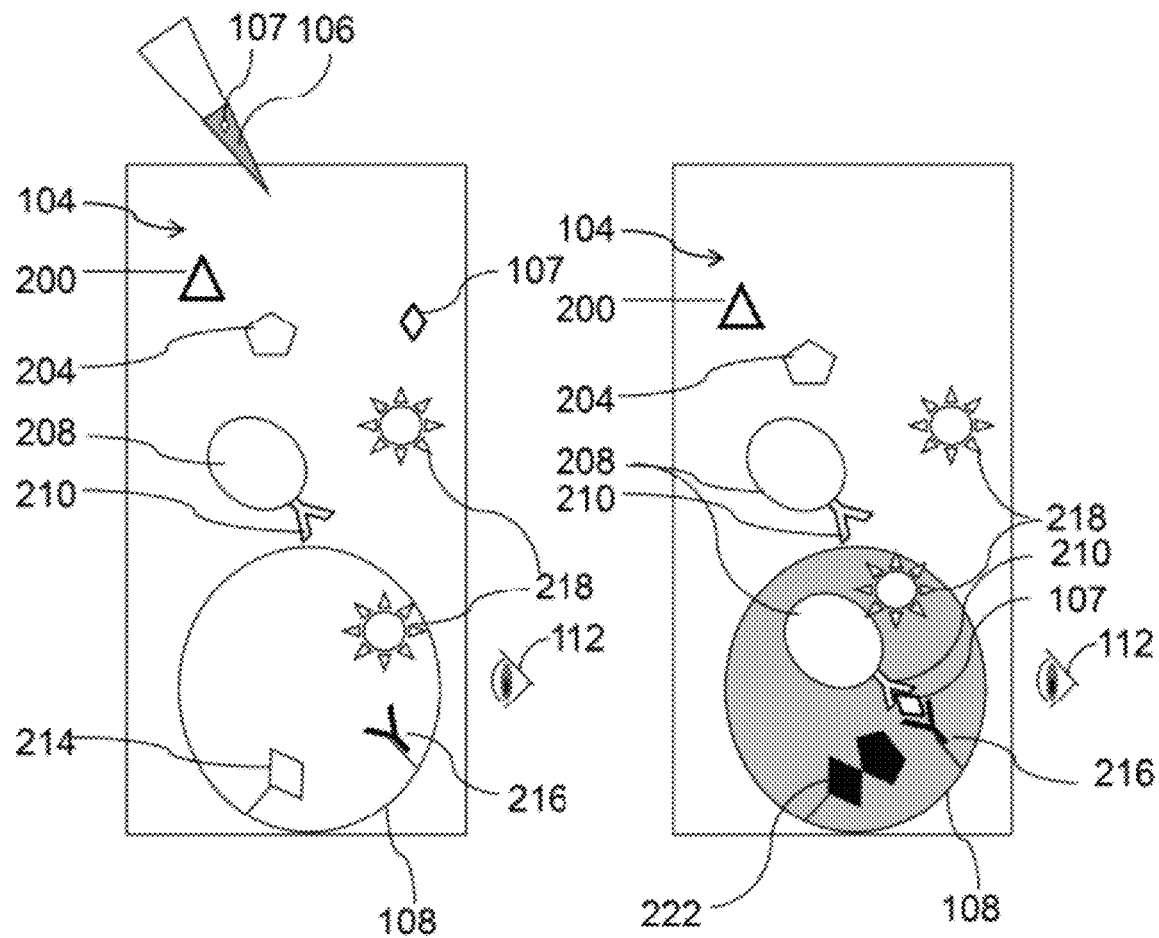

TWO-PHASE OPTICAL ASSAYS FOR ANALYTES OF NO INTRINSIC OPITCAL CONTRAST

REFERENCE TO RELATED APPLICATION

The present application claims the priority to U.S. Provisional Application Ser. No. 61/371,684 Aug. 7, 2010, which is herein incorporated by reference in its entirety

FIELD OF THE INVENTION

The invention relates to quantification of analytes in a sample, more specifically to methods for assaying analytes of no optical contrast via an optical contrast complex.

BACKGROUND OF THE INVENTION

One of the greatest challenges to modern biomedical science is the ability to measure minute amounts of specific molecules in samples with limited availability. U.S. Pat. No. 4,857,454 teaches an assay method using an antibody/analyte/second antibody-enzyme conjugate microparticle system. The method requires washing the microparticles to remove non-captured materials, a step that introduces a great deal of variability. In addition, the color generated in the microparticles diffuses into the solution surrounding the microparticles, which dilutes the signal representing the quantity of analyte. U.S. Pat. Nos. 5,674,699 and 7,851,229 disclose a method for assaying Hemoglobin A1c in a blood sample using a two-phase optical assay. The prior art of the two-phase assay only discloses a single functional component on the microparticle, a ligand to capture the analyte. The analyte Hemoglobin A1c in the blood sample is intensely colored and abundant enough in the erythrocytes (about 2 μM even in non-diabetics) so that it is feasible to use the method disclosed therein for measuring Hemoglobin A1c. The methods disclosed in those two patents however cannot perform an assay for an analyte that has insufficient or no inherent optical contrast. For example, cytochrome C is colored but the levels in cells are too low to be measured by using the methods disclosed therein.

Therefore, a previously unaddressed need exists in the art to address the aforementioned deficiencies and inadequacies, especially in connection with measuring analytes with no intrinsic optical properties.

SUMMARY OF THE INVENTION

In one aspect, the invention relates to a method of performing a two-phase optical assay of one or more than one analyte without intrinsic optical contrast in a sample, comprising:
 (a) providing functionalized microparticles, the functionalized microparticles each comprising immobilized two or more than two functional components,
  wherein the two or more than two functional components are chosen from:
   (i) a first ligand;
   (ii) a color forming substrate;
   (iii) an enzyme for generating an intermediate reagent; and
   (iv) a fluorochrome,
  and wherein at least one of the two or more than two functional components is the first ligand;
 (b) providing a buffer solution and one or more than one functional component, the one or more than one functional component being the same or different from the two or more than two functional components immobilized to the microparticle in step (a) and being chosen from:
   (i) an optical signal amplifier attached to a second ligand;
   (ii) a color forming substrate;
   (iii) a co-substrate;
   (iv) a blocked substrate or a blocked coupler;
   (v) a precursor substrate;
   (vi) a coupler;
   (vii) an enzyme for generating an intermediate reagent; and
   (viii) a fluorochrome.
 (c) admixing a sample comprising one or more than one analyte without intrinsic optical contrast with the buffer solution, the one or more than one functional component, and the functionalized microparticles in a container to form a two-phase suspension with the functionalized microparticles suspended in the buffer solution;
 (d) allowing the one or more than one analyte to bind the first ligand and/or the second ligand attached to the optical signal amplifier and to develop an optical signal in the microparticles;
 (e) measuring the optical signal of the two-phase suspension having the functionalized microparticles suspended in the buffer to obtain a first measurement;
 (f) allowing the functionalized microparticles to settle to the bottom of the container to obtain a microparticle-rich phase at the bottom of the container and a substantially microparticle-free phase above the microparticle-rich phase;
 (g) measuring the optical signal of the microparticle-rich phase to obtain a second measurement; and
 (h) calculating a relationship between the first and second measurements to determine the concentration of the one or more than one analyte.

In another aspect, the invention relates to a kit for performing a two-phase optical assay, the kit comprising:
 a) functionalized microparticles, the functionalized microparticles each comprising immobilized two or more than two functional components, wherein the two or more than two functional components are chosen from:
   (i.) a first ligand;
   (ii) a color forming substrate;
   (iii) an enzyme for generating an intermediate reagent; and
   (iv) an fluorochrome,
   and wherein at least one of the two or more than two functional components is the first ligand
 b) a buffer solution; and
 c) one or more than one functional component, the one or more than one functional component being the same or different from the two or more than two functional components immobilized to the microparticles in a) and being chosen from:
   (i) an optical signal amplifier attached to a second ligand
   (ii) a color forming substrate;
   (iii) a co-substrate;
   (iv) a blocked substrate or a blocked coupler;
   (v) a precursor substrate;
   (vi) a coupler;
   (vii) an enzyme for generating an intermediate reagent; and
   (viii) a fluorochrome.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1A depicts a container with a cap at the beginning of a two-phase optical assay.

FIG. 1B shows the container of FIG. 1A while measuring the optical signal of suspended microparticles.

FIG. 1C shows the container of FIG. 1B while measuring the optical signal of settled microparticles.

FIG. 1D shows a cap (a cover for a container) with multiple compartments.

FIG. 4A is a schematic representation of functional components at the beginning of the assay according to one embodiment of the invention.

FIG. 4B is a schematic of FIG. 4A at the end of the assay according to one embodiment of invention.

DETAILED DESCRIPTION OF THE INVENTION

Definitions

Figures 2A, 2B, 2C:
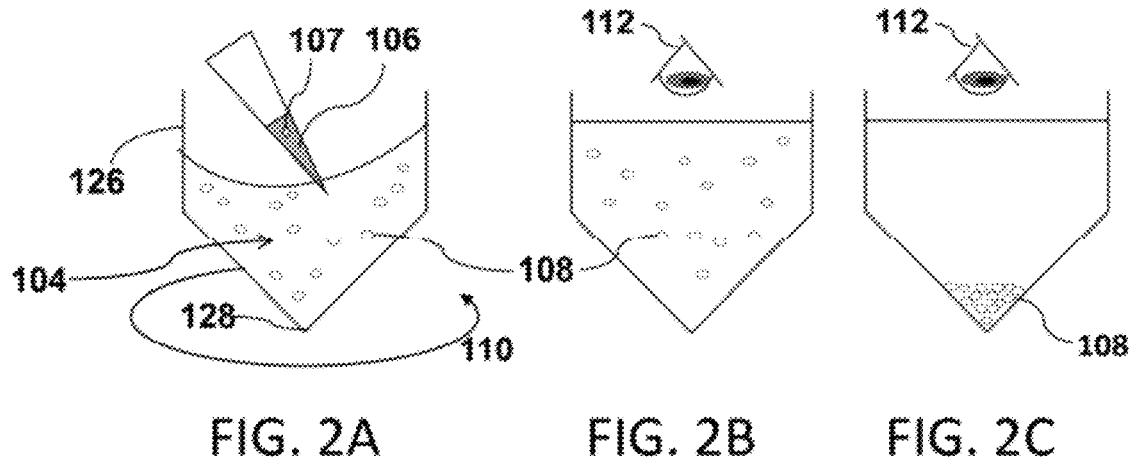
FIG. 2A depicts a pointed well at the beginning of a two-phase optical assay.
FIG. 2B shows the pointed well of FIG. 2A while measuring the optical signal of suspended microparticles.
FIG. 2C shows the pointed well of FIG. 2B while measuring the optical signal of settled microparticles.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification. Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "microparticles" means spheres or pieces of solid or semisolid phase 40 to 200 microns in diameter. The "solid" phase can be either continuous or contain pores. The "solid" phase may be composed of a wide variety of materials, such as but not limited to agarose, cellulose, acrylimide, latex, or silica. When in an aqueous suspension the porous microparticles may contain only a few percent of the named solid matter. The remainder of the space in the microparticle is the same as buffer that surrounds the solid phase. The terms microparticles and beads may be used interchangeably in this invention.

The term "phase" means a collection of matter with uniform physical properties. Two phases include a solution phase and a solid phase, each of which may be either continuous or discontinuous. For example, a solid phase may be discontinuous due to the presence of pores.

The term "optical phase" means a physical state, either liquid or particulate that may be subjected to optical analysis. In a two phase system in the same container a means of separating phases in position or in time is required for operation of the invention. A suspension is a special case which is the combination of the solution phase with the solid phase. A suspension may act as an imperfect representation of either the solution phase or the solid phase together with at least one pure phase to achieve the purposes of the two phase optical assay.

The term "substantially transparent" means that the microparticles are clear, having as little effect on light transmission and scattering as possible. They therefore cannot be opaque, as is the case with magnetic microparticles.

The "terms functionality" and "functional component" mean any individual element of the assay that performs a discreet activity or undergoes a defined change in the assay, including, but not limited to a ligand characteristic, a molecule with constant and stable fluorescence, a molecule that changes fluorescence according to the concentration of analyte, a molecule having reactive qualities of a photographic developer in that it responds to the oxidative amplifier, a molecule having qualities like a photographic color coupler, or an amplifier molecule that directly or indirectly enhances the color contrast. A combination of functionalities may be required in order to achieve specificity of optical contrast for the intended analyte assay. When immobilized to the microparticle, a functionalized microparticle is formed.

The term "contrast" means the property of a substance that causes a change in the amount of a light signal detected, such as, but not limited to, absorbance, phosphorescence, fluorescence, quenching of a fluorescent molecule's emission and light scattering.

The term "analyte of no optical contrast" or "analyte without optical contrast" or "analyte without contrast" includes analytes that have insufficient optical contrast to be measured by optical systems at the concentrations expected in commonly used samples. For example, cytochrome C is colored, but not sufficiently to uniquely detected without using impractically large amounts of sample. This invention addresses the substitution of a contrast that is quantitatively or qualitatively related to such an analyte with insufficient contrast.

The term "fluorochrome" refers to any compound that absorbs a photon of light at one wavelength and re-emits it at another one in a detectable manner.

The term "substrate" means any molecule or part of a molecule that is acted on by an enzyme. This includes both compounds that are chromogenic, such as oxidizable developers, and co-substrates that participate in an enzyme reaction but do not have colored product.

The term "color forming substrate" means any molecule that takes part in the formation of a color contrast as a result of the action of an enzyme on the said molecule. The action of the enzyme on said molecule may be sufficient to form color without subsequent reactions. Action of the enzyme on the substrate may be an activation of the said molecule allowing it react with a different molecule, such as a coupler, or further react with a second and more molecules of the same species to form color. Some of the color forming substrates also have properties of a photographic developer.

The term "co-substrate" means a chemical compound that participates in an enzymatic reaction, but does not form a colored product. For example, hydrogen peroxide is a co-substrate for horseradish peroxidase.

The term "developer" means a chemical compound, either free in solution or attached to a solid phase that is susceptible to oxidation and participates in the generation of a color as a result of the oxidation. In this patent oxidation of the developer may directly generate a color or it may generate color by coupling to a chromogenic coupler as a result of prior oxidation. The term developer includes photographic developers.

The term "coupler" means a compound that reacts with the activated developer and completes color formation. Hence, such couplers may be termed "chromogenic couplers" because they generate a color.

The term "a blocked coupler" is a compound which when unblocked can act as a coupler. Thus a blocked coupler needs to be unblocked before it can be used as a coupler. An example of a blocked coupler includes, but not limited to, 1-phospho-2,4-dichloro-1-naphthol, which can be deblocked by a phosphatase and form 2,4-dichloro-1-naphthol. The 2,4-dichloro-1-naphthol can be used as a coupler to react with a compound such as peroxidase activated 2-chloro-phenylene-1,4-diamine to form a colored product.

The term "Dimerizing substrate" refers to a substrate that can dimerize or polymerize in the presence of an enzyme. 1-naphthol is an example of a dimerizing or polymerizing substrate.

The term "immobilized substrate" means a molecule that is covalently attached to the microparticles prior to the beginning of the assay procedure (as part of the manufacturing process). As with other substrates already defined, immobilized substrates are molecules that are altered or activated by the action of an enzyme. Under defined conditions, an immobilized substrate may also be a color forming substrate and will then be designated as a "immobilized color forming substrate"

The term "precursor substrate" means a compound that does not participate directly in the optical signal generating reaction, but instead acts as a substrate for an enzyme that produces a product that is directly involved in the optical signal generating reaction. An example would be glucose being used by glucose oxidase to produce hydrogen peroxide, which is in turn used by horseradish peroxidase as a co-substrate in an optical signal generating reaction.

The term "blocked substrate" means a compound that otherwise would be useful as a substrate or coupler (previously defined) except that a key part of the molecule involved in its use has a substituent added to it. The substituent is removable by a specific enzyme, liberating the substrate or coupler needed for the color forming reaction. An example of a compound with blocking group and its specific enzyme is 1-naphthyl phosphate and alkaline phosphatase, producing the color forming substrate 1-naphthol. The term "hydrolases" refers to enzymes that cleave a chemical bond by the addition of water. Examples include, but not limited to, phosphatases, esterases, and glycosidases.

The term "optical signal amplifier" means a component with catalytic qualities that increases the rate of a chemical reaction that produces a color contrast.

The term "enzyme for generating an intermediate reagent" means any enzyme that uses a substrate to produce a product that participates in the formation of an optical contrast. Examples of enzyme for generating an intermediate reagent include, but are not limited to, glucose oxidase, which uses the precursor substrate, glucose, to produce hydrogen peroxide, and alkaline phosphatase, which uses the blocked substrate, 1-naphthyl phosphate to produce 1-naphthol.

The term "fluorescence difference signal" refers to the difference in fluorescence signal intensity between the end and beginning of the microparticles settling.

The term "fluorescence ratio" refers to the ratio of the fluorescence at the beginning versus the fluorescence at the end of microparticle settling, or vice versa. The numerator and denominator of the ratio or both may contain offset factors defined by a assay user. A separate, user-defined offset may also be applied to the entire ratio.

The term "ligand" shall generally mean one component of a pair of molecules that have strong attraction for each other. The pair is a ligand pair. Examples of ligand pairs include, but are not limited to antibodies and their target antigens, lectins and their target carbohydrates, receptors and their target molecules, and ion exchange substituent. For the purpose of this invention, the first ligand is attached to the microparticle. The second ligand starts the assay in the solution and has the optical signal amplifier attached to it. Either or both the first and the second ligand with the optical signal amplifier attached to it can form ligand pairs with the analyte in the sample. The relationships will be made clearer in the definition of the three assay types provided below.

The term "analtye" means a substance in a sample that is to be measured. It is the second ligand of a ligand pair, the first ligand of the pair being either the first ligand or the second ligand with the optical signal amplifier attached to it. It may also be an inhibitor of the formation of a ligand pair between the first ligand and the second ligand with the optical signal amplifier attached to it.

The term "competitive assay" means a ligand configuration is being used in which the analyte is the same as either the first or the second ligand with the optical signal amplifier attached to it. Two different arrangements are possible. When the first ligand is the same as the analyte, the analyte in the sample occupies binding sites on the second ligand with the optical signal amplifier attached to it and prevents the second ligand with the optical signal amplifier attached to it from binding to the first ligand. When the second ligand with the optical signal amplifier attached to it is the same as the analyte, the analyte in the sample occupies binding sites first ligand and prevents the binding of the second ligand with the optical signal amplifier attached to it. In both cases, the amount of second ligand with the optical signal amplifier attached to it is bound to the functionalized microparticle is inversely proportional to the amount of analyte added to the assay.

The term "sandwich assay" means a ligand configuration is being used in which analyte binds to both the first ligand and the second ligand with the optical signal amplifier attached to it, acting as a bridge between the two. The amount of second ligand with the optical signal amplifier attached to it in the functionalized microparticle is therefore proportional to the amount of analyte added to the assay.

The term "sero-positive assay" means a ligand configuration is being used in which the first ligand is capable of binding a broad class of molecules, of which the analyte is a member. The analyte acts as a bridge between the first ligand and the second ligand with the optical signal amplifier attached to it which is specific to the analyte to be measured.

The invention relates to a system in which uncolored analytes bind to microparticles and an amplification system generates a localized quantifiable optical signal for measuring the concentration of the analytes. It was discovered that multiple functional groups can be attached to a microparticle used in a two phase optical system in a way allowing the formation of a new signal generating optical product. The chemistry of photographic developers and couplers has been in use since the early part of the 20$^{th}$ century (Bent R L, et al. J. Am. Chem Soc 73 3100-3124, 1951). Many photographic developers contain primary and secondary amines that act as substrates for oxidative enzymes such as peroxidase (Conyers S M and Kidwell D A Analytical Biochemistry 192(1):207-211, 1991) (Pearse AGE *Histochemistry: theoretical and applied 2$^{nd}$ Edition* 1960, Pp 512-515), the products of which initiate coupling reactions similar to those seen with activated silver ions. It was found that the phenylene diamine derivatives behave as developers when immobilized to the microparticles if photographic-type coupler compounds such as phenols or naphthols were supplied from the solution. This is different from color photography chemistry, in which the coupler is immobilized in the film and the developer is a common, soluble reagent that permeates the film layers to where the color-specific reactions with couplers take place. It was also found that immobilization of ligands such as antibodies on the microparticle concentrates the analyte and other functional components out of the solution in a complex that generates an optical signal localized to the microparticle. When the microparticles and solution containing the coupling reagents are used in a two-phase configuration, a quantitative assay can be achieved in which an analyte without optical contrast can be measured in a single container without any separation steps, markedly reducing the possibility of operator error.

FIG. 1A shows that the sample 106 containing an analyte 107 to be measured is added to a container 100, filled with a solution 104 and microparticles 108, covered with a cap 102, and mixed 110 for a period optimal for the specific assay. All reactions take place within the closed container 100 without any further additions or washes. After mixing 110, measurements are made with one or more optical sensors 112 when the microparticles 108 are in suspension (FIG. 1B) and also after the microparticles 108 are settled (FIG. 1C). The measurement when the microparticles 108 are in suspension acts as a reference measurement for calculation of algorithms. If more than one optical sensor is used (FIG. 1C), one optical sensor 112 has its light path in line with the settled microparticles 108 and is used for measuring the optical signal generated in the microparticles 108 due to the presence of analyte 107 in the sample 106. The other optical sensors 114 are located at other parts of the container 100 and can be used to test for completion of settling and as a reference measurement in the calculation of algorithms.

In one embodiment, the cap 102, is divided into multiple compartments (FIG. 1 D) to separate functional components that are incompatible with each other during storage. Raised partitions 116 and partitions formed by indentations 118 into the wall of the cap 120 act as barriers to form compartments 122 where the incompatible functional components may be stored separately from each other in a chemically and mechanically stable form 124. At the beginning of the assay, preincubation steps may be performed in one compartment of the cap. The cap is sealed to the container with the functional components facing inward. The capped container is then mixed by inversion, allowing the contents of the cap to mix with the rest of the assay. The mixing also begins the timing of the assay.

FIG. 2A shows an embodiment of the assay that uses an open container such as a microtiter plate well 126 with a pointed bottom 128. The sample 106 containing the analyte 107 is added to the a well 116 containing the solution 104 and microparticles 108, mixed 110 for an assay-specific time, and measured while microparticles 108 are suspended (FIG. 2B) and settled (FIG. 2C) with at least one optical sensor 112. In this way, a two-phase optical assay may be performed in a conventional device such as a microtiter plate reader without the need for an instrument specifically designed for doing the two-phase optical assays.

Figure 3:
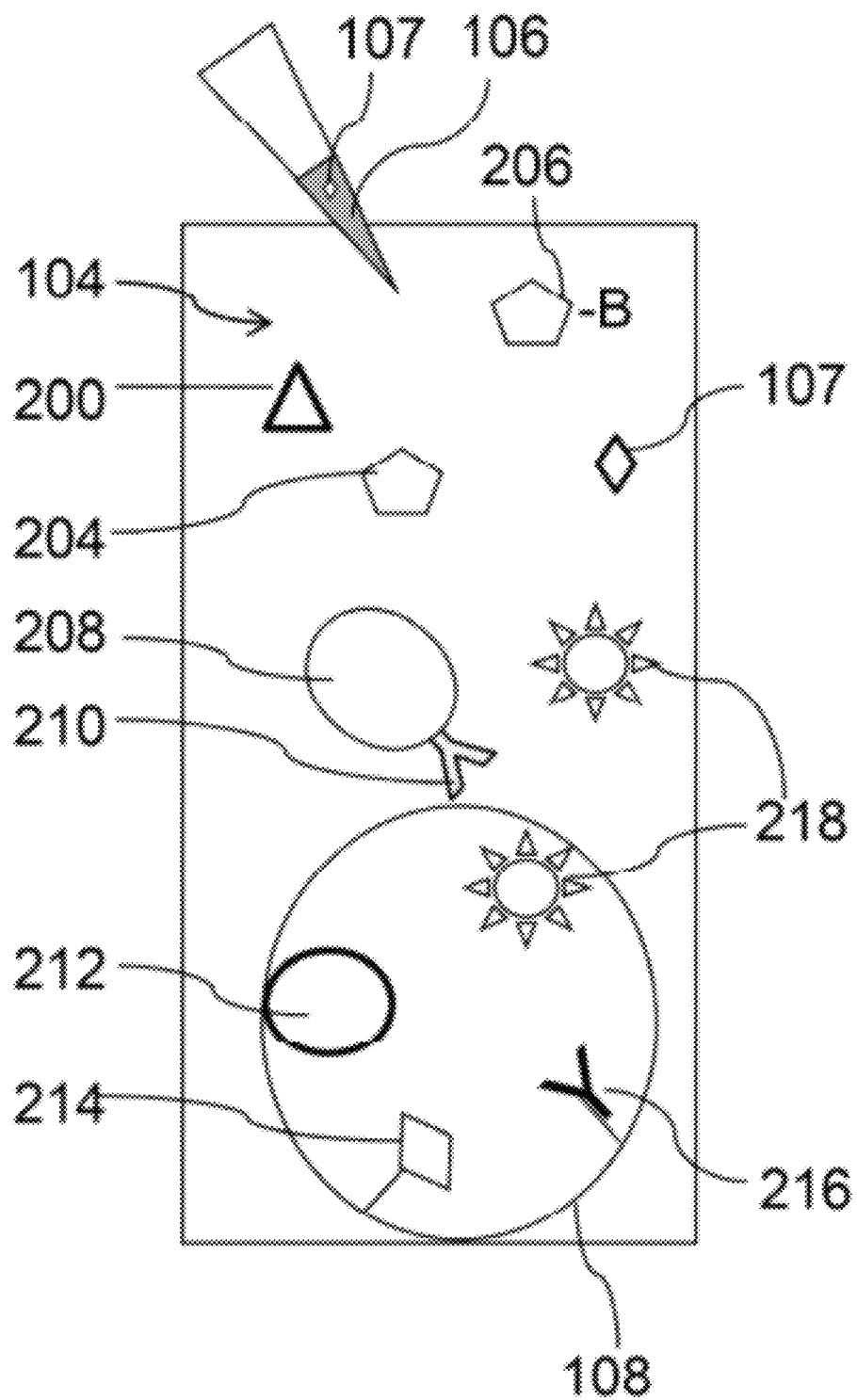
FIG. 3 is a schematic representation of functional components for a two phase optical assay measuring analytes with no intrinsic optical signal at the beginning of the assay.

The two-phase optical assay according to this invention requires the assembly of functional components on the microparticle in order to generate an optical signal for measuring the analyte 107 in the sample 106. Depending on the specific needs of the assay, the number of functional components and their distributions in the microparticles and solution may vary. FIG. 3 shows a schematic depiction of all the types of functional components, whether they are used in a specific assay or not. At minimum, two functional components need to be immobilized to the microparticle 108: One is a first ligand 216 to selectively concentrate the remaining functional components in the solution 104 into the microparticle 108. The other immobilized functional component is a part of an optical signal-generating system and may be chosen from, but not limited to, a fluorochrome 218, enzyme for generating an intermediate reagent 212 and a color forming substrate 214. Functional components that may be distributed in the solution 104 include, but are not limited to, enzyme co-substrates and/or their precursors 200, coupling agents 204 chromogenic substrates or couplers that may comprise removable blocking groups 206, fluorochromes 218, and a second ligand 210 with the optical signal amplifier 208 attached to it.

FIG. 4A illustrates one embodiment of the invention. A microparticle 108 comprising the first ligand 216 and color forming substrate 214 are suspended in a solution 104 within a container 100. A sample 106 containing an analyte 107 is added into the solution 104 within the container 100. The analyte 107 binds to the first ligand 216 attached to the microparticle 108 and is thus concentrated in the microparticle 108. The analyte 107 bound to the immobilized first ligand 216 attracts from solution the second ligand 210 with the optical signal amplifier 208 attached to it, thus assembling the equivalent of the sandwich in an ELISA assay. The result is that the signal amplifier 208 is concentrated into the microparticle 108 in proportion to the analyte 107 concentration in the sample 106. A co-substrate and/or its precursor 200 and a coupling agent 204 which are also present in the solution 104 diffuse into the microparticle 108, leading to the formation of an optical signal-generating product 222 in the microparticle 108 (FIG. 4B). The optical signal-generating product 222 is formed only in the microparticle 108 because the microparticle 108 is the only place where the co-substrate and for its precursor 200, the coupler 204, the immobilized color forming substrate 214, and the second ligand 210 with the optical signal amplifier 208 attached to it are all present together. In this case, the immobilized color forming substrate reacts to form a colored optical signal-generating product 222, the light absorbance of which may be measured with an optical sensor 112 at a designated wavelength.

In some cases, an additional functional component, a fluorochrome 218, present in the microparticle 108 or in the solution 104, may be used in the assay system. In this case, the optical signal-generating product 222 acts as a fluorescence quencher. A loss of fluorescence is measured with an optical sensor 112 by calculating the difference from a control.

Alternatively, an optical signal-generating product 222 may be luminescent or phosphorescent, and the light produced thereby may be directly measured with an optical sensor 112.

Figures 5A, 5B:
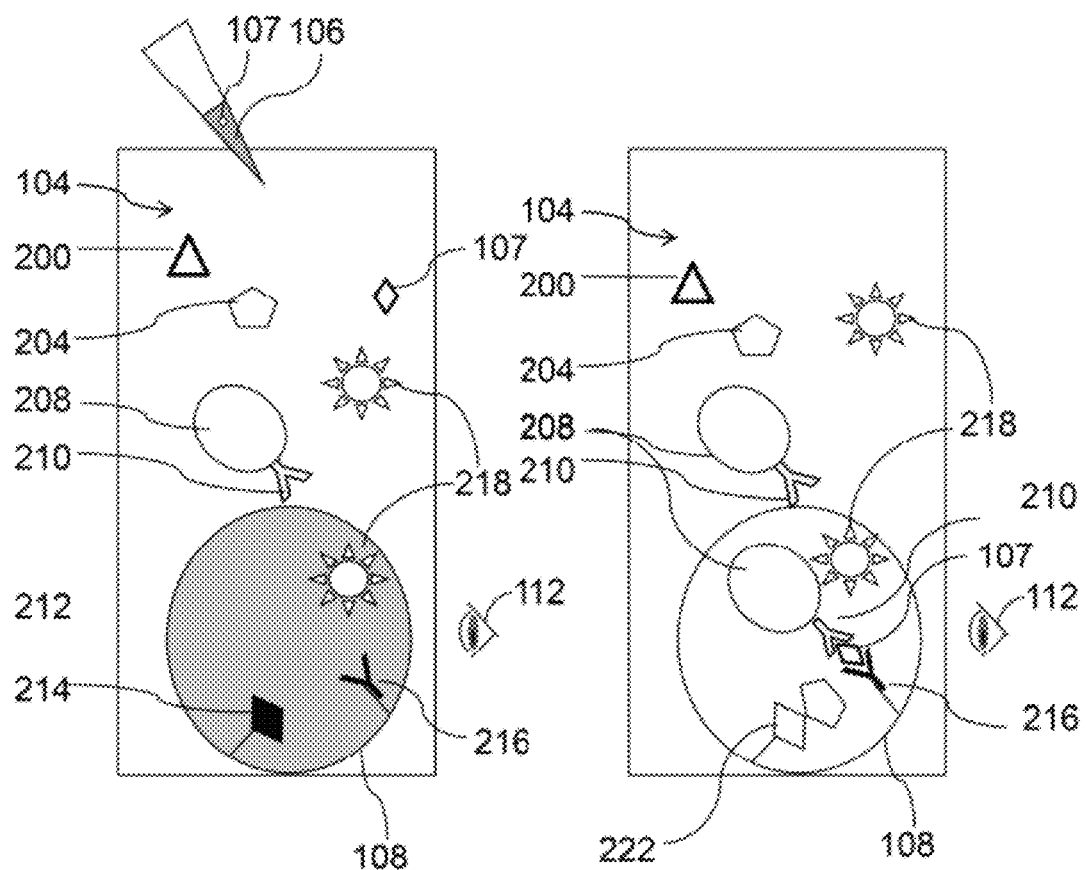
FIG. 5A is a schematic representation of functional components at the beginning of the assay according to another embodiment of the invention.
FIG. 5B is a schematic of FIG. 5A at the end of the assay according to another embodiment of the invention.

In another embodiment of the invention, the immobilized substrate 214 may start out being colored (FIG. 5A). In this case, the presence of an analyte 107 causes the colored immobilized substrate 214 to react and form an optical signal-generating product 222, leading to a change of color or a bleaching (i.e., loss of color contrast) of the microparticle 108 (FIG. 5B). A decrease in light absorbance may be directly measured with an optical sensor 112. In the situation where a fluorochrome 218 is also present in the microparticle 108 or in the solution 104, the change of color or bleaching (i.e., loss of color) of the microparticle 108 may be measured with an optical sensor 112 as a loss of quenching (i.e., an increase in fluorescence) to reflect the presence of the analyte 107.

Figures 6A, 6B:
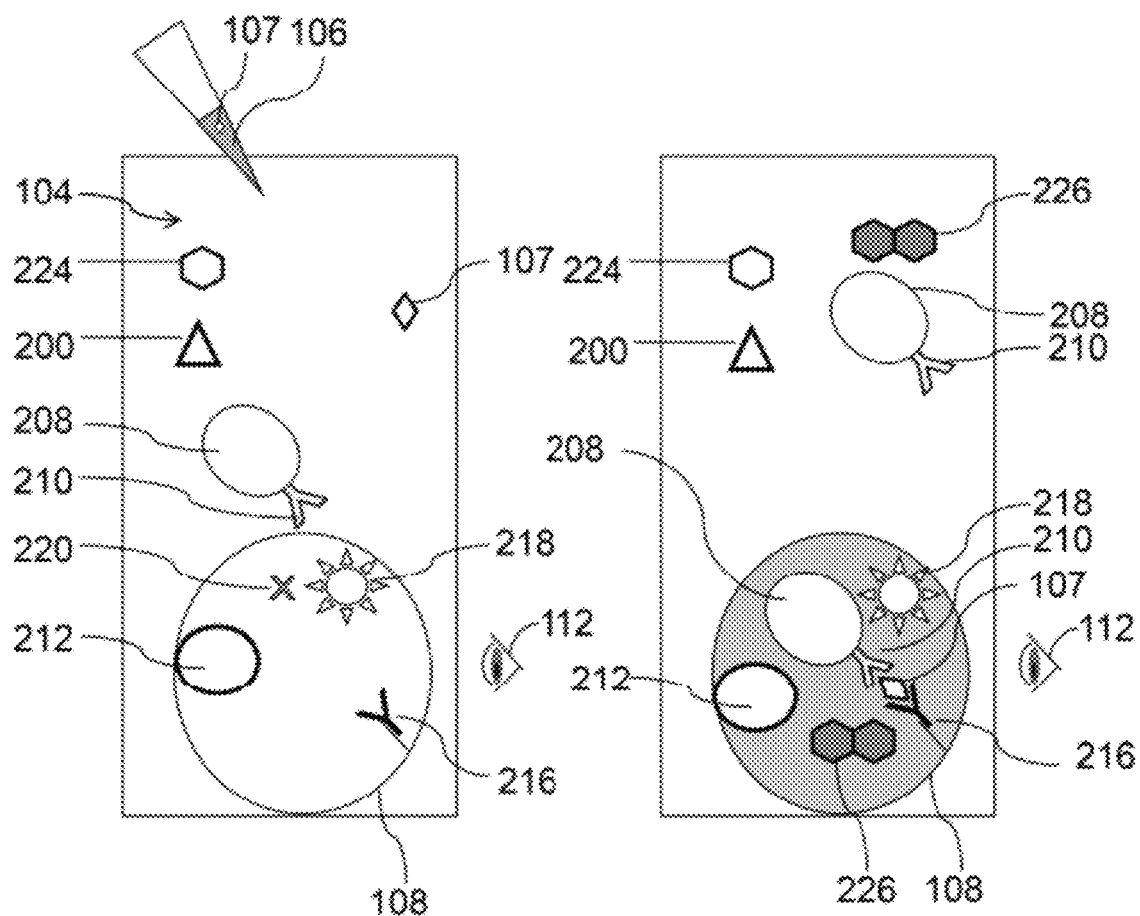
FIG. 6A is a schematic representation of functional components at the beginning of the assay according to another embodiment of the invention.
FIG. 6B is a schematic of FIG. 6A at the end of the assay according to another embodiment of the invention.

In yet another embodiment of the invention, the assay uses a solution 104 containing a co-substrate and/or its precursor 200, a second ligand 210 with the optical signal amplifier 208 attached to it, and a chromogenic substrate 224 that is capable of dimerizing or polymerizing (FIG. 6A). In this case there is an immobilized first ligand of a ligand pair 216 on the microparticle, 108, but an immobilized color forming substrate 214 is not needed. Instead, a fluorochrome 218 and/or an enzyme for generating an intermediate reagent 212 are immobilized to the microparticle 108 as the second and third functional groups. The second ligand 210 with the optical signal amplifier 208 attached to it will generate dimerizing or polymerizing optical signal-generating product 226 both in the solution 104 and when concentrated in the microparticle by the by formation of a complex with the immobilized first ligand 216 and the analyte 107 (FIG. 6B). The result is a dilute non-specific background of dimerizing or polymerizing optical signal-generating product 226. The immobilized fluorochrome 218 forces the signal measured at the optical sensor 112 to be related to the presence of microparticles 108. The use of an immobilized enzyme for generating an intermediate reagent 212 and a precursor substrate 200 or blocked substrate 206 restricts the formation an intermediate reactant 220 to the microparticle 108 in the vicinity of the immobilized first ligand 216, the location where the signal due to the presence of an analyte 107 in the sample 106 would be measured. In such fashion, the nonspecific dimerized or polymerized optical signal generating product 226 is minimized to the point where it can easily be dealt with by calculation.

Additional embodiments are achieved by varying the configuration of the ligands and their relationship to the optical signal amplifier. As shown in table 1, competitive, sandwich, and sero-positive assays are feasible using the optical signal generation functional components described above.

TABLE 1

| Assay type | First ligand on microparticle | Second ligand in solution | Analyte bound to | Reaction product formed in the microparticle |
|---|---|---|---|---|
| Competitive | Identical to the analyte | Different from the analyte | Second ligand | Inversely proportional to analyte |
|  | Different from the analyte | Identical to the analyte | First ligand | Inversely proportional to analyte |
| Sandwich | Different from the analyte | Different from the analyte and the immobilized ligand | First & second ligand | Proportional to analyte |
| Sero-positive | Different from the analyte, selective for a broad class of molecules | Different from the analyte and the immobilized ligand | First and second ligand | Proportional to analyte |

In one aspect, the invention relates to a method of performing a two-phase optical assay of one or more than one analyte without intrinsic optical contrast in a sample, comprising:

(a) providing functionalized microparticles, the functionalized microparticles each comprising immobilized two or more than two functional components,
   wherein the two or more than two functional components are chosen from:
   (i) a first ligand;
   (ii) a color forming substrate;
   (iii) an enzyme for generating an intermediate reagent; and
   (iv) a fluorochrome,
   and wherein at least one of the two or more than two functional components is the first ligand;

(b) providing a buffer solution and one or more than one functional component, the one or more than one functional component being the same or different from the two or more than two functional components immobilized to the microparticle in step (a) and being chosen from:
   (i) an optical signal amplifier attached to a second ligand;
   (ii) a color forming substrate;
   (iii) a co-substrate;
   (iv) a blocked substrate or a blocked coupler;
   (v) a precursor substrate;
   (vi) a coupler;
   (vii) an enzyme for generating an intermediate reagent; and
   (viii) a fluorochrome.

(c) admixing a sample comprising one or more than one analyte without intrinsic optical contrast with the buffer solution, the one or more than one functional component, and the functionalized microparticles in a container to form a two-phase suspension with the functionalized microparticles suspended in the buffer solution;

(d) allowing the one or more than one analyte to bind the first ligand and/or the second ligand attached to the optical signal amplifier and to develop an optical signal in the microparticles;

(e) measuring the optical signal of the two-phase suspension having the functionalized microparticles suspended in the buffer to obtain a first measurement;

(f) allowing the functionalized microparticles to settle to the bottom of the container to obtain a microparticle-rich phase at the bottom of the container and a substantially microparticle-free phase above the microparticle-rich phase;

(g) measuring the optical signal of the microparticle-rich phase to obtain a second measurement; and (h) calculating a relationship between the first and second measurements to determine the concentration of the one or more than one analyte.

In one embodiment of the invention, step (d) causes the one or more than one functional component in the buffer solution to indirectly attach to the functionalized microparticles through the analyte that is bound to the immobilized first ligand on the functionalized microparticles.

In another embodiment of the invention, the step (d) causes the analyte to compete for binding to the first or second ligand, preventing the second ligand from binding to the immobilized first ligand on the functionalized microparticles.

In another embodiment of the invention, the optical signal amplifier attached to the second ligand is an enzyme.

In another embodiment of the invention, the enzyme is a peroxidase.

In another embodiment of the invention, the functionalized microparticles in step (a) each comprise the immobilized first ligand and the immobilized fluorochrome.

In another embodiment of the invention, the functionalized microparticles in step (a) each comprise the immobilized first ligand and the immobilized color forming substrate.

In another embodiment of the invention, the functionalized microparticles in step (a) each further comprise the immobilized fluorochrome.

In another embodiment of the invention, the color forming substrate comprises an aromatic compound having two or more than two amine functional groups, one of the two or more than two amine functional groups being attached to the microparticles to form the functionalized microparticles.

In another embodiment of the invention, the aromatic compound is one chosen from 2-chloro-phenylene-1,4-diamine, diaminobenzidine, ortho-dianisidine, 1,4-diamino-naphthalene and derivatives thereof.

In another embodiment of the invention, the functionalized microparticles each comprise the immobilized first ligand, the immobilized color forming substrate, the immobilized fluorochrome, and the immobilized enzyme for generating the intermediate reagent.

In another embodiment of the invention, the admixing step causes the color forming substrate to dimerize or polymerize and form a colored product.

In another embodiment of the invention, the functionalized microparticles in step (a) each further comprise the immobilized fluorochrome.

In another embodiment of the invention the immobilized enzyme for generating the intermediate reagent comprises an oxidase other than peroxidase, and produces hydrogen peroxide after the admixing step.

In another embodiment of the invention, step (b) provides more than one functional component, which comprises:

(i) the optical signal amplifier attached to the second ligand, wherein the optical signal amplifier comprises an enzyme;
(ii) the co-substrate; and
(iii) the blocked substrate.

Further in another embodiment of the invention, the immobilized enzyme for generating the intermediate reagent comprises a hydrolase.

Yet in another embodiment of the invention, the functionalized microparticles in step (a) each comprise
(i) the first ligand;
(ii) optionally the color forming substrate;
(iii) the enzyme for generating an intermediate reagent; and
(iv) optionally the fluorochrome.

In another aspect, the invention relates to a kit for performing a two-phase optical assay, the kit comprising:
(a) functionalized microparticles, the functionalized microparticles each comprising immobilized two or more than two functional components, wherein the two or more than two functional components are chosen from:
  (i) a first ligand;
  (ii) a color forming substrate;
  (iii) an enzyme for generating an intermediate reagent; and
  (iv) a fluorochrome,
  and wherein at least one of the two or more than two functional components is the first ligand
(b) a buffer solution; and
(c) one or more than one functional component, the one or more than one functional component being the same or different from the two or more than two functional components immobilized to the microparticles in a) and being chosen from:
  (i) an optical signal amplifier attached to a second ligand
  (ii) a color forming substrate;
  (iii) a co-substrate;
  (iv) a blocked substrate or a blocked coupler;
  (v) a precursor substrate;
  (vi) a coupler;
  (vii) an enzyme for generating an intermediate reagent; and
  (viii) a fluorochrome.

In one embodiment of the invention, the kit further comprises a container or vessel adapted for optical measurements.

In another embodiment of the invention, the container or the vessel is closable with a cover, or is open without a cover and has a point at the bottom.

Further in another embodiment of the invention, the cover has multiple compartments for segregating and storing the one or more than one functional component.

Yet in another embodiment of the invention, the kit further comprises an insert with instructions.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Assay Using Microparticles with an Immobilized Substrate and a Ligand

The microparticles were SEPHAROSE® CL6B (General Electric). This resin has a large pore size (molecular weight cutoff about $10^6$ daltons) which will allow space for both ligands such as antibodies and large antigens. It settles completely within a period of about 2 minutes in aqueous suspensions, and is nearly optically transparent. The microparticles were activated as follows: they were washed in distilled water and incubated with ten volumes of 70 mM sodium periodate for 1 hour to oxidize vicinal diols to aldehydes. Schiff's reagent (Sigma, catalog number 3952016) was added to a small volume of microparticles after the reaction to confirm they were activated with aldehydes. Ethylene glycol was added to 100 mM for 30 minutes to use up any unreacted periodate and the microparticles were washed with 10 volumes of water on a Büchner funnel. These activated microparticles were ready for attachment of various functional components according to the invention.

To attach the fluorochrome functional component, the microparticles were resuspended in 10 volumes of 0.1 N sulfuric acid for 30 minutes to make them strongly acidic. After replacing the preincubation with more sulfuric acid, the fluorochrome, Lucifer Yellow Carbohydrazide (CH) was added to a final concentration of 30 µM and incubated with the microparticles for 1 hour. This resulted in fluorescently labeled activated microparticles, which were then washed with water on a Buchner funnel and preincubated with 10 volumes of 50 mM sodium acetate buffer, pH 6.0 for one hour to bring the pH up for subsequent steps.

The next functional component to be attached to the fluorescently labeled microparticles was an immobilized color forming substrate. The aromatic diamine compound 2-chloro-phenylene-1,4-diamine was used as an immobilized color forming substrate to demonstrate the properties of immobilized compounds with photographic developer properties as peroxidase substrates. In this example, it is immobilized by means of a Schiff reaction that is reduced with cyanoborohydride. One of the two primary amines therefore becomes secondary because it is involved in linkage to the microparticle. The fluorescently labeled activated microparticles were incubated for 1 hour in ten volumes of acetate buffer, pH 6.0 containing 20 mM cyanoborohydride and 30 µM 2-chloro-phenylene-1,4-diamine.

The first ligand, the protein Avidin, was the last functional component to be added. It was added last in the order to avoid damage to the Avidin with the harsh treatments in the previous steps that could potentially inactivate the protein. Briefly, after washing with water, the microparticles were incubated for 1 hour in twice their volume of acetate buffer, pH 6.0 containing 20 mM cyanoborohydride and 0.1 mg egg white Avidin per ml of microparticles. This resulted in microparticles labeled with a first ligand, an immobilized color forming substrate and a fluorochrome. They were extensively washed with water to remove excess first ligand and stored in an acetate buffer at 4° C. until used. For comparison, microparticles without the immobilized color forming substrate 2-chloro-phenylene-1,4-diamine were produced, containing only the immobilized fluorochrome, Lucifer Yellow, and the first ligand, Avidin.

The properties of the Lucifer Yellow/2-chloro-phenylene-1,4-diamine/Avidin microparticles were tested by incubating them with biotinylated horseradish peroxidase. In this case, the analyte is biotin. It is conjugated to horseradish peroxidase (HRP). The conjugation is an irreversible binding step, making the HRP both an optical signal amplifier enzyme and a second ligand. The biotinylated HRP was incubated with the microparticles for 30 minutes in 50 mM Borate pH 8.0, 0.1% TRITON™ X-100. Biotin binds tightly to the immobilized Avidin on microparticles. Specificity was demonstrated by preabsorption with 100 µM free biotin for 10 minutes before adding the biotinylated HRP. No washes were performed. The coupler 2,4 dichloro 1-naphthol was then added to microparticles made with immobilized Lucifer Yellow, 2-chloro-phenylene-1,4-diamine, and Avidin. For comparison, a dimerizing substrate, 1-naphthol, was added to the microparticles made without the immobilized substrate 2-chloro-phenylene-1,4-diamine. The color forming reaction was initiated by the addition of Barium peroxide which acts as a source for the co-substrate, hydrogen peroxide. The capped cuvettes were rotated end over end for 7 minutes to allow the contents to mix and the contrast reaction to develop. At the end of this time, the sample rotation stopped with the cuvettes vertical and the microparticles were allowed to settle in front of the fluorescence detector for three minutes. The first measurement was made with the microparticles fully suspended. Measurements were collected at 5.8 second intervals during the microparticle settling. The fluorescence measurements during the settling were used to determine when the microparticles were completely settled, Criteria such as a change in fluorescence between measurements of 1% or less can be used to determine when the microparticles are completely settled. The two critical measurements to retain for calculation purposes are the one at the beginning, when the microparticles are suspended, and the end, when the microparticles are fully settled.

Figure 7:
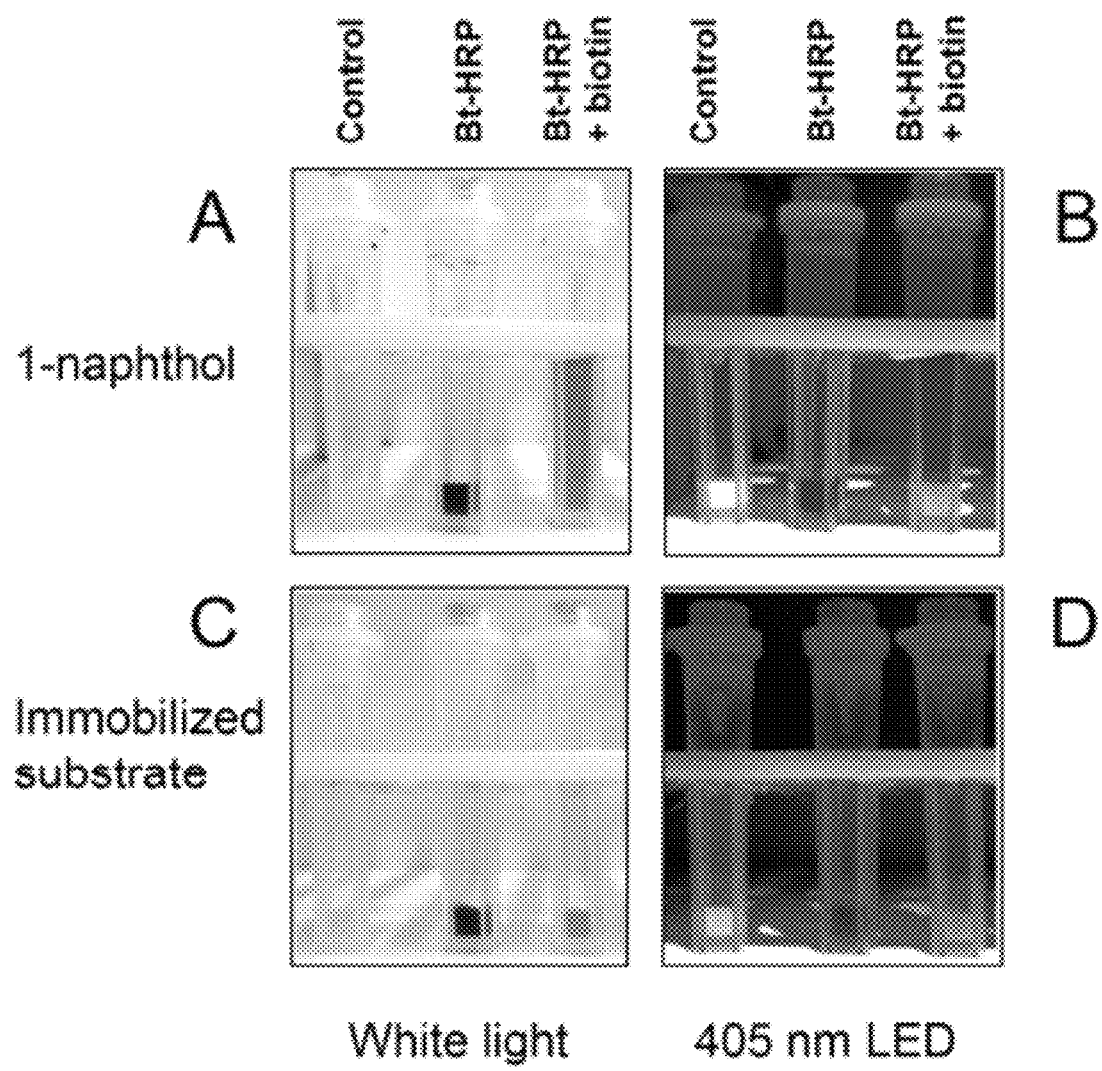
FIG. 7A is a photograph showing containers of settled microparticles at the end of an assay performed with 1-naphthol as a substrate viewed in white light.
FIG. 7B is a photograph showing containers of FIG. 7A viewed with a 405 nm LED.
FIG. 7C is a photograph showing containers of settled microparticles at the end of an assay performed with an immobilized substrate viewed in white light.
FIG. 7D is a photograph showing containers of FIG. 7C viewed with a 405 nm LED.
Figure 8:
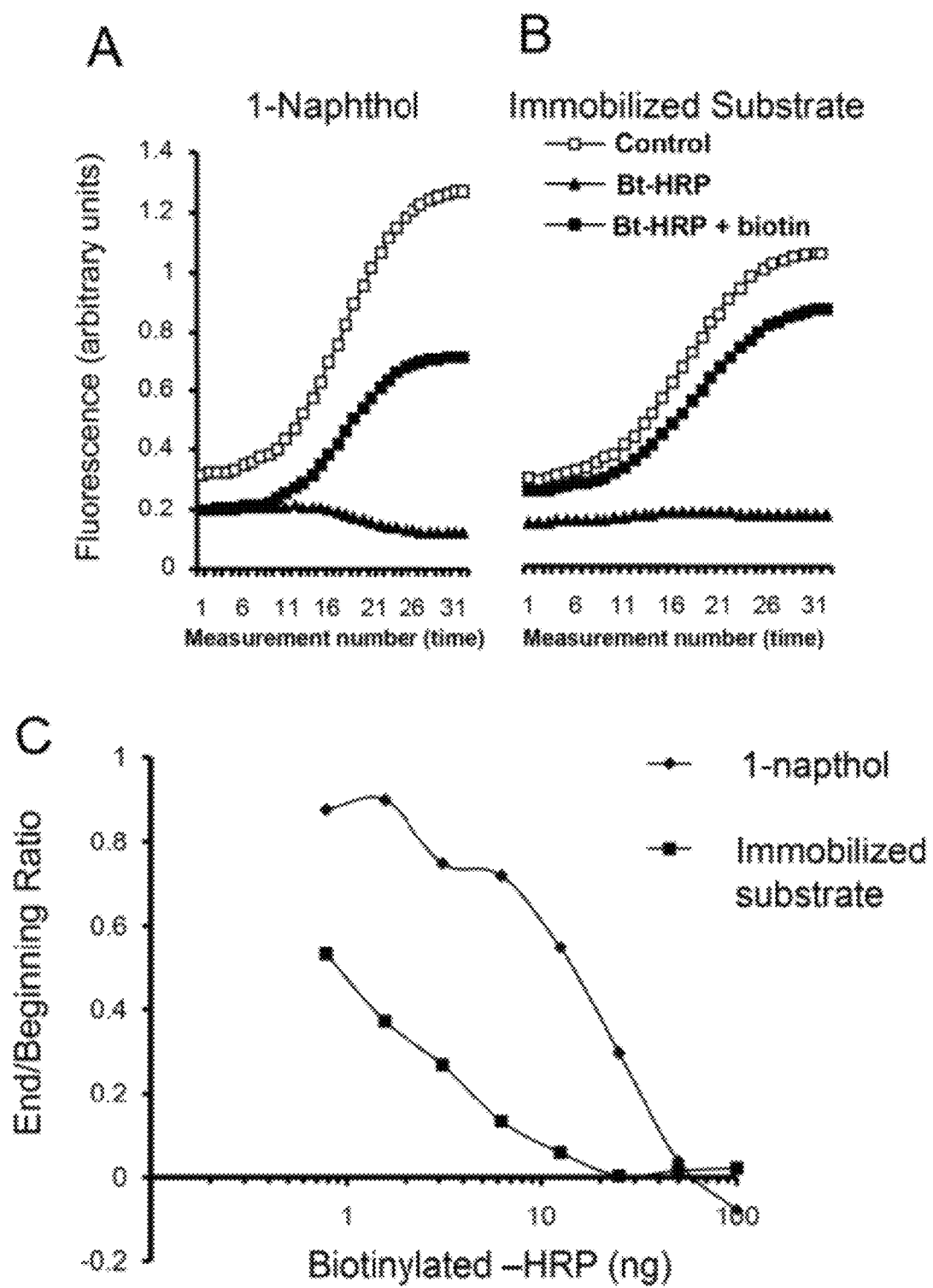
FIG. 8A is a graph showing the fluorescence signals of microparticles of FIG. 7B measured during the process of settling. Open squares indicate the control microparticles, the filled triangles the addition of biotinylated-HRP and the filled squares preincubation with free biotin before adding biotinylated-HRP.
FIG. 8B is a graph showing the fluorescence signals of microparticles of FIG. 7D measured during the process of settling. Open squares indicate the control microparticles, the filled triangles the addition of biotinylated-HRP and the filled squares preincubation with free biotin before adding biotinylated-HRP.
FIG. 8C is a graph showing the effect of biotinylated HRP (an analyte) concentrations on the fluorescence signal intensity of the settling microparticles. Diamonds measurements made with 1-naphthol, squares measurements made with the immobilized substrate.

In the absence of the peroxide co-substrate, the fluorescence increases as the microparticles settle. When peroxide is present, the colored coupling reaction quenches the fluorescence signal. Preabsorption with biotin reversed the quenching. As shown in FIG. 7A-B, when 1-naphthol, a dimerizing or polymerizing substrate, was used the microparticles turned a dark blue-black color and lost fluorescence. FIGS. 8A-B shows an increase in fluorescence signal intensity as the microparticles settled and its quenching by the peroxidase reaction. There was, however, additional blue color in the solution, indicating that the 1-naphthol had acted as a peroxidase substrate for the residual biotinylated HRP in the solution (FIG. 7A, third tube). In contrast, the coupling of 2,4 chloro-1-naphthol to the immobilized color forming substrate 2-chloro-phenylene-1,4-diamine (FIGS. 7C-D) produced an intense blue color in the microparticles and the solution remained clear, indicating that peroxidase reaction was confined to the microparticles. The blue color formed by the immobilized color forming substrate was not extractable by the organic solvent DMSO, confirming that it was covalently bound to the microparticles. A dilution curve of the biotinylated HRP (FIG. 8C) shows that the method yielded quantitative results. The 2,4 dichloro 1-naphthol coupled to 2-chloro-phenylene-1,4-diamine (immobilized color forming substrate) was approximately 10-fold more sensitive as a substrate system than the 1-naphthol (a dimerizing substrate). In this example, the output of the optical detector was expressed as the difference in fluorescence between the end and beginning of the settling curve. This data transformation is a simple way of applying an internal reference to the data which minimizes the effect of nonspecific quenching.

Example 2

Characterization of Immobilized Substrate Reactions

Figure 9:
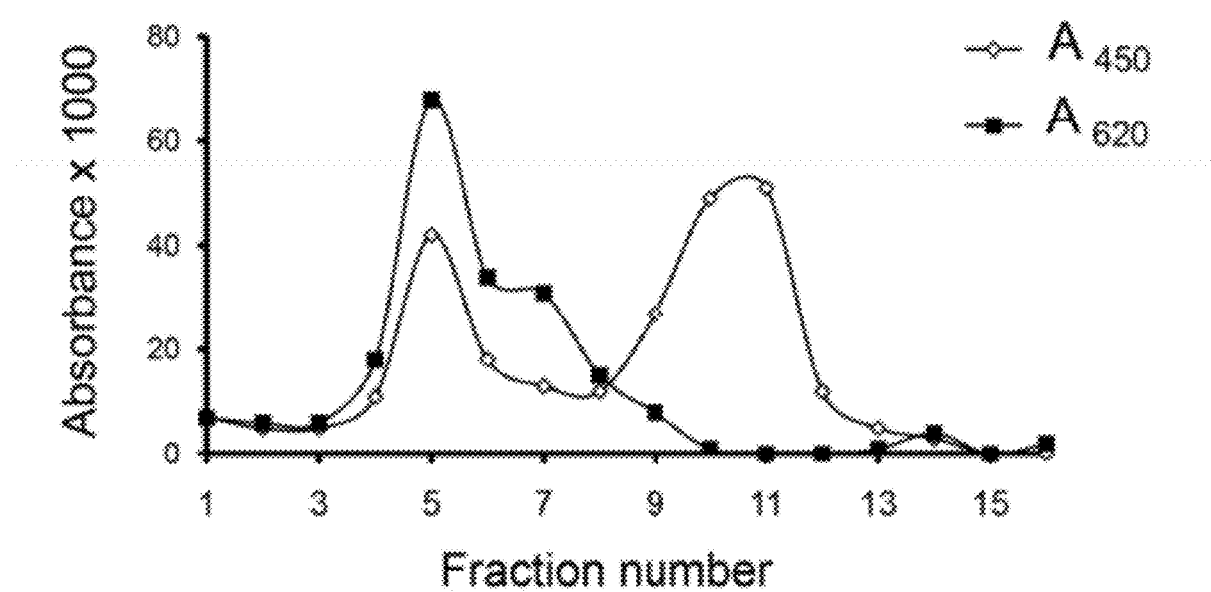
FIG. 9 is a graph showing the light absorbance measurements of chromatographic column fractions obtained from a separation of a soluble dextran bearing optical signal product. Open diamonds indicate the absorbance measurements at 450 nm, filled squares absorbance measurements at 620 nm.

As proof that a coupling reaction had taken place, soluble dextran was used to distinguish between a soluble reaction that had been trapped inside the microparticle and a truly immobilized reaction. Dextran with an average molecular weight of 500,000 daltons was modified with Lucifer Yellow and 2-chloro-phenylene 1,4 diamine as described above. The modified dextran was then exposed to the coupler 4-methoxy phenol, the co-substrate hydrogen peroxide, and the signal amplifier horseradish peroxidase for 20 minutes before being chromatographed on a 0.7×5 cm SEPHADEX® G-100 column. The 0.5 ml fractions were measured for Lucifer Yellow and the blue reaction product by their absorption at 405 and 620 nm, respectively. The results are seen in FIG. 9. The Lucifer Yellow eluted as a major peak at the excluded volume of the column indicating it was immobilized to the dextran. A second peak eluting much later was observed, consistent with free Lucifer Yellow not attached to the dextran. The absorbance for the peroxidase reaction product co-eluted with the Lucifer Yellow at the excluded volume, indicating that it was immobilized to the dextran. The peroxidase-induced color was therefore the product formed from immobilized 2-chloro-phenylene 1,4 diamine and the 4-methoxy phenol in solution.

An additional proof that a distinct immobilized reaction is taking place is a comparison the color of the reaction products in solution and immobilized to the microparticles. The color forming substrate 2-chloro-phenylene 1,4 diamine was used in both solution reactions and immobilized to the microparticles. The 2-chloro-phenylene-1,4-diamine was immobilized to microparticles as described in Example 1 and 0.5 mM solutions of 4-chloro resorcinol, 1-naphthol, 2,4 dichloro 1-naphthol, and 1-(hydroxyphenyl) 1H tetrazol-5-thiol were used as couplers for peroxidase reactions. For comparison, solution assays were performed using 100 µl of 1 mM of the couplers was mixed with 100 µl of 1 mM 2-chloro-phenylene-1,4-diamine and 10 µl of 3% hydrogen peroxide. About 1 µg of HRP was added, the wells mixed, and the color was observed after 30 minutes at room temperature.

Microparticle immobilized and solution color forming substrate assays were performed in parallel using the four couplers. Table 2 shows that all four couplers formed a reaction product with 2-chloro-phenylene 1,4 diamine, both in solution and immobilized to the microparticle. The color of the product, however, was quite different, indicating that the properties of the diamine with two primary amines was different from that of the compound with one of the amines now secondary because of attachment to the microparticle. Other diamine compounds that have been successfully immobilized to the microparticle and produce coupling reactions include ortho-di-anisidine, 3,3'-diamino benzidine, 1,4 diamino naphthalene, and 1,1'-binaphthyl-2,2'-diamine (data not shown).

TABLE 2

|  | 4-Chloro Resorcinol | 1-(hydroxyphenyl) 1H tetrazol-5-thiol | 1-Naphthol | 2,4 Dichloro 1-Napthol | 4-phenoxy phenol |
|---|---|---|---|---|---|
| Solution reaction | Red | Yellow | Violet | Purple | Purple |
| Immobilized reaction | Aquamarine | Green | Blue-black | Blue | Red |

Example 3

Competitive Two-Phase Immunoassay

The fluorochrome Lucifer Yellow and the first ligand human serum album were covalently attached to Periodate-treated CL6B as described above. In this example, the albumin is both an immobilized first ligand and an analyte. The immobilized albumin in the microparticle binds the second ligand (an antibody) with the signal amplifier (HRP) attached and concentrates it in the microparticle. A limiting amount of the second ligand with the optical signal amplifier attached was used. When the analyte albumin is in the sample, it binds to the second ligand with the optical signal amplifier attached in the solution and prevents second ligand with the optical signal amplifier attached from binding to the immobilized albumin. The result is that the quenching of the fluorescence signal is inversely that proportional to the amount of albumin in the sample.

To perform the assay, microparticles were precisely aliquoted in 50 mM Imidizole 0.1% TRITON™ X-100, pH 7.5 assay buffer containing the dimerizing or polymerizing peroxidase substrate 1-naphthol and stored at 4° C. until used. Barium peroxide was a source of the co-substrate hydrogen peroxide. It was stored as a viscous slurry in polyethylene glycol in a compartment of a multi-compartmentalized cap. The second ligand with the optical signal amplifier attached to it, a dried mouse monoclonal antibody against human serum albumin conjugated to HRP, was stored in second compartment of the multi-compartmentalized cap.

The assay was initiated by adding the sample to the cap compartment containing the antibody-HRP conjugate. The sample and antibody-HRP conjugate were mixed and incubated together for 5 minutes, allowing time for the antibody to come back into solution and bind to the albumin in the sample. The cap was then fastened to the cuvette with the side containing the sample and the other compartments facing inward. The entire assembly was inverted several times to mix the contents of the cap with those of the cuvette and inserted into the detection instrument, where it was rotated end over end for 7 minutes. This rotation period allowed time for the antibody-HRP conjugates that were not bound to albumin in the sample to bind to the microparticle and generate an optical signal product with the 1-naphthol. The sample rotation then stopped and the microparticles were allowed to settle in front of the fluorescence detector for three minutes. Fluorescence measurements were made at 5.8 second intervals during the settling period.

Figure 10A:
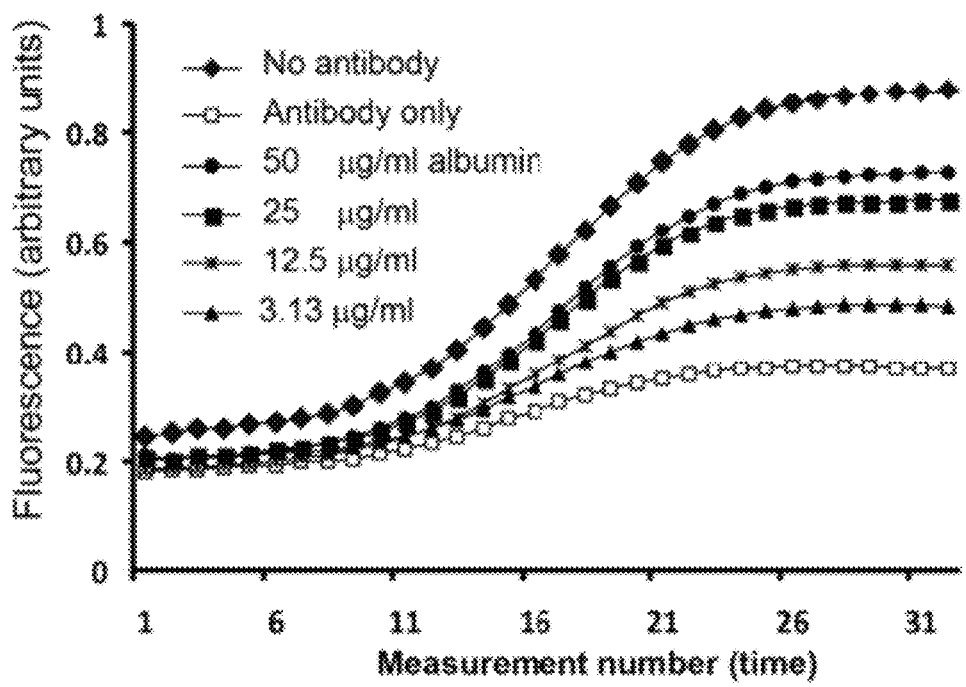
FIG. 10A is a graph showing the fluorescence signal intensity of settling microparticles in a fluorescence quenching assay for human serum albumin.
Figure 10B:
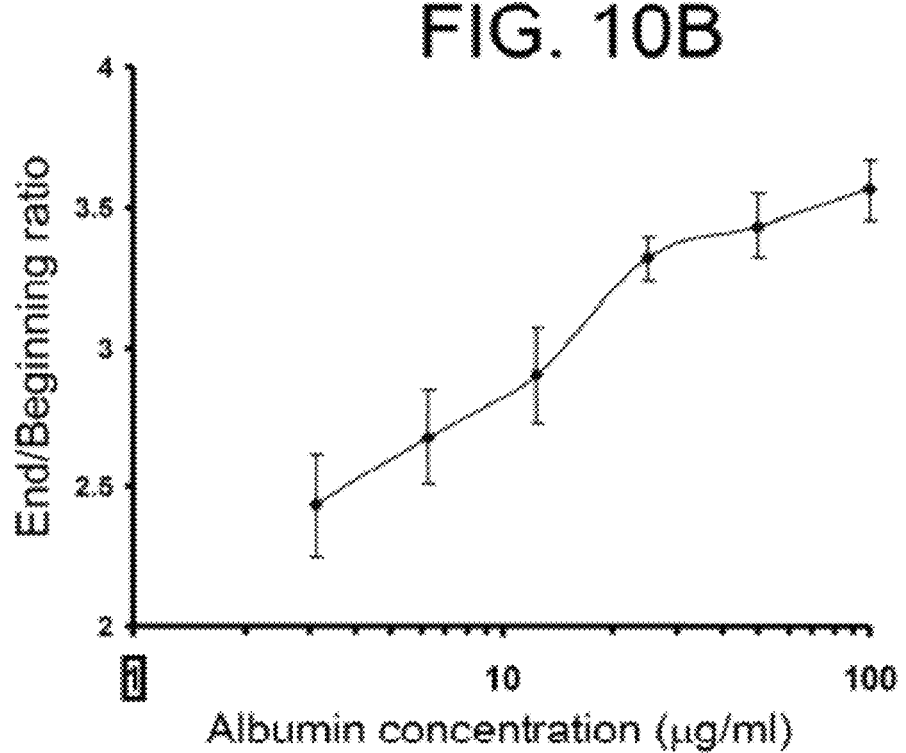
FIG. 10B is a graph showing a concentration-response curve for the assay of FIG. 10A

As can be seen from FIG. 10A, in the absence of antibody and albumin the microparticles settle in the light path of the detector and the fluorescence increases over time. When the HRP conjugated antibody is added in the absence of albumin, a great deal of conjugate binds to the microparticle and generates a color reaction that quenches the fluorescence. Albumin in the sample occupies a fraction of the binding sites, preventing them from binding to the microparticle and generating the quenching reaction. The amount of albumin in the sample is therefore directly related to the loss of quenching (an increase in fluorescence) in the settling curve. In the assay presented, the quenching of the fluorescence signal in the absence of albumin is nearly complete. When concentrations of albumin greater than 50 µg per ml are present in the sample, the antibody is nearly saturated with albumin in solution and quenching is minimal. The range of quenching constitutes 50 percent of the total fluorescence increase as the microparticles settle, indicating that the assay is robust. The working range of albumin concentrations that can be measured is 3-25 µg/ml, including both the normal albumin level and the threshold for clinical microalbuminuria (Gross, J L et al. Diabetes Care 28 (1): 164-76, 2005), (Mattix H J et al. J. Am. Soc. Nephrol. 13: 1034-1039, 2002). An albumin standard curve is shown in FIG. 10B calculated using the ratio method (see the next paragraph). The data represents 6 curves for a single lot of microparticles measured over an 8 week period. The coefficients of variation were between 3% and 7% over the entire curve, indicating that the variability of the test is low enough to give clinically interpretable data.

A complicating factor in the analysis of the fluorescence quenching is that 1-naphthol is a dimerizing or polymerizing peroxidase substrate for both the HRP-antibody conjugate bound to the microparticle and that remaining in solution. As the HRP bound to the microparticle decreases, the amount in solution increases, creating a uniform background quenching that is present throughout the settling curve. The entire settling curve is offset to some degree. The degree of offset is also dependent on the amount of analyte in the solution, making a simple correction factor impossible. A very useful data transformation that eliminates the problem is to calculate the ratio of the fluorescence at the beginning to end (or vice versa) of the settling curve. Since the background quenching is a fixed percentage of both the numerator and denominator of the ratio, it drops out of the equation—for example [(8*0.6)/(3*0.6)=8/3=1.6]—and simplifies the data analysis. Use of ratio in this way is only valid if the source of the fluorescence is the solution or the microparticles, but not in both.

Example 4

Two-Phase, Two Antibody Sandwich Immunoassay

Figure 11A:
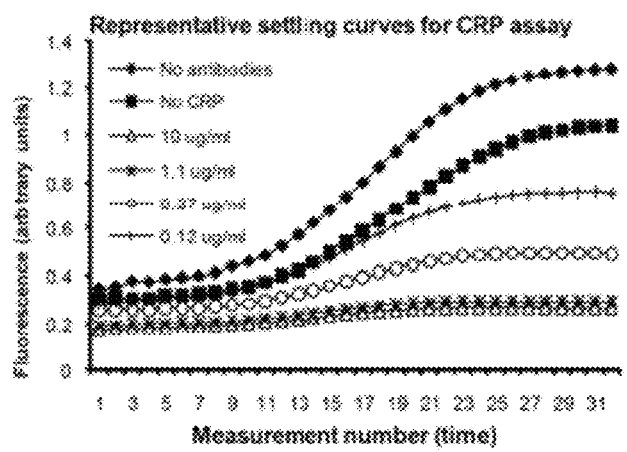
FIG. 11A is a graph showing the fluorescence signal intensity of settling microparticles in a fluorescence quenching assay for C Reactive Protein (CRP).
Figure 11B:
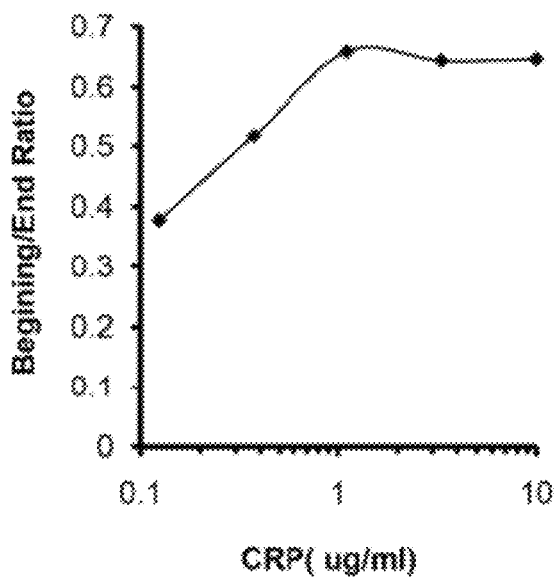
FIG. 11B is a graph showing a concentration-response curve for the assay of FIG. 11A.
Figure 11C:
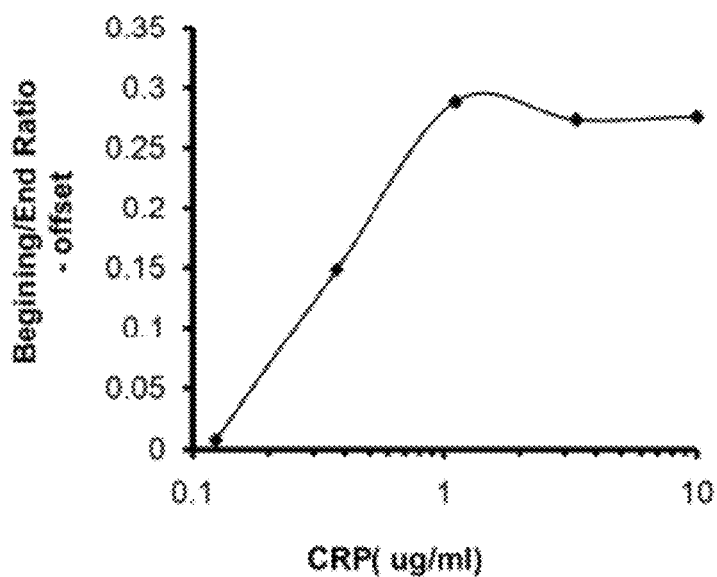
FIG. 11C is a graphs showing the concentration response curve for the assay of FIG. 11B with an offset subtracted.

A two-phase immunoassay for C-reactive protein was performed SEPHAROSE® CL6B microparticles were modified with Lucifer Yellow CH and Avidin. Biotinylated goat anti-CRP antibodies were incubated with the microparticles and washed. This incubation generates the immobilized first ligand, the anti-CRP antibody immobilized to microparticles. Various concentrations of CRP were added to the cuvette and incubated for an hour, followed by the addition of a single concentration the second ligand with the optical signal amplifier attached, mouse anti-CRP conjugated to HRP. No wash steps were preformed. Barium peroxide and 1-napthol were then added to initiate contrast development. After tumbling for 7 minutes the microparticles were allowed to settle and optical measurements were obtained at 5.8 second intervals over three minutes. The quenching increased with the concentration of the CRP added to the assay (FIG. 11A). A concentration/response curve was generated by plotting the CRP concentration versus the fluorescence ratio (FIG. 11B). Note that in order to have the graph presented as saturation curve, the beginning divided by the end ratio is presented, the reciprocal of the ratio used albumin assay in FIG. 10B. In FIG. 11C, an offset has been subtracted from the entire ratio to remove the baseline. The sensitivity was more than adequate to detect CRP at the clinical threshold of 1 to 3 µg/ml (Pepys M B and Hirschfield G M, J. Clin. Invest. 111(12): 1805-1812, 2003).

Example 5

Two-Phase Sero-Positive Immunoassay

An immunoassay for detecting a specific antibody in a serum sample was demonstrated using microparticles with enough immobilized Protein G to bind all the immunoglobins in a small sample. Since the antibody subclass generated against an antigen in a disease can vary between individuals, sero-positive tests are usually expressed in terms of units of a reference serum. The actual concentration of antibody against the target antigen is unknown. To circumvent this problem, an artificial system was used. A normal rabbit serum and defined amount of an antibody against a specific protein, a mouse monoclonal antibody against human serum albumin, were added to the assay. The amount of monoclonal antibody was determined using human serum albumin conjugated to HRP as the second ligand with the optical signal amplifier attached to it.

Lucifer Yellow, 2-chloro-phenylene-1,4-diamine, and Protein G were sequentially immobilized on the microparticles as described above. The Protein G was immobilized at a concentration of 0.5 mg/ml of microparticles for three hours in the presence of 20 mM sodium cyanoborohydride in 50 mM sodium acetate buffer, pH 6.0. The HRP-human serum albumin conjugate was produced using the Bioconjugate Toolkit™ as described by the manufacturer (Pierce).

To perform the assay, the Lucifer Yellow/2-chloro-phenylene-1,4-diamine/Protein G microparticles were precisely aliquoted in a cuvette with a 50 mM imidizole 0.1% TRITON™ X-100 buffer, pH 7.0. Ten microliters of normal rabbit serum, ten microliters of a mouse monoclonal antibody against human serum albumin (clone 15C7, Abcam) and 1 µg of the HRP-human serum albumin conjugate were added to the container. After closing with a cap, the container was mixed by rotation for 20 minutes. After adding the coupler 4-methoxy phenol to 1 mM and the co-substrate hydrogen peroxide to 7 mM, the contents of the cuvette was mixed by inversion several times and inserted into the detection instrument, where it was rotated end over end for 7 minutes to allow time for color development. The sample rotation then stopped and the microparticles were allowed to settle in front of the fluorescence detector for three minutes. Fluorescence measurements were made at 5.8 second intervals during the settling period.

Figure 12A:
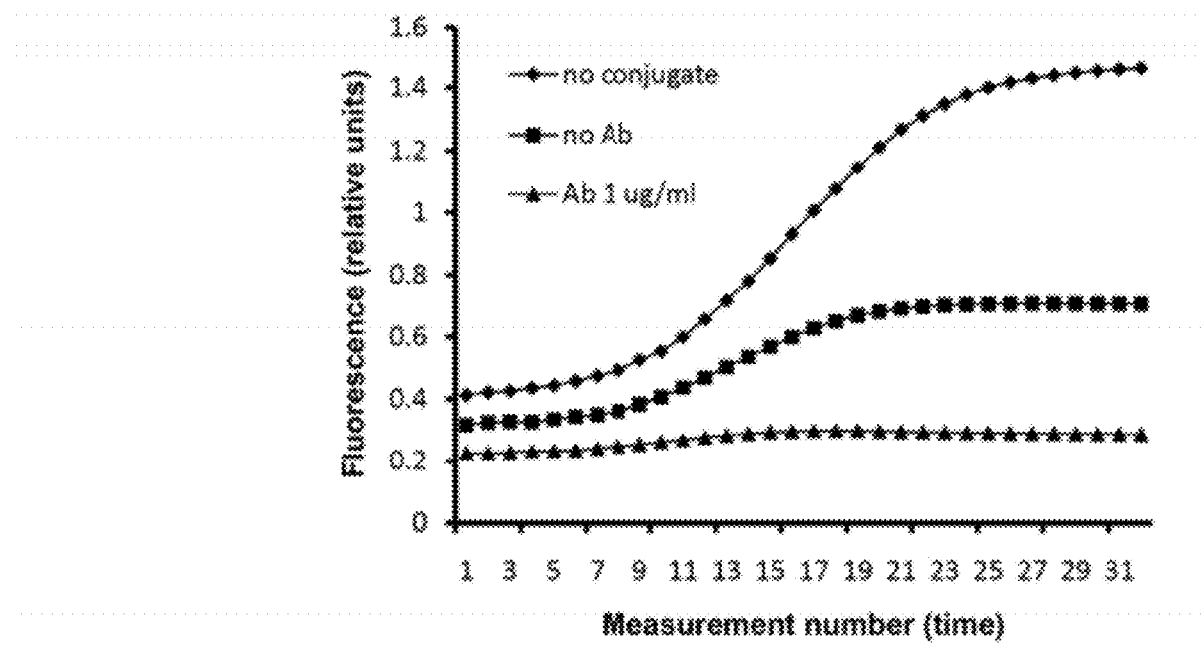
FIG. 12A is a graph showing the fluorescence signal intensity of settling microparticles in a model of a fluorescence quenching sero-positive assay. Diamonds indicate microparticles measured without conjugate added, squares microparticles measured with conjugate added, and triangles microparticles measured with conjugate and 1 µg/ml of mouse anti-albumin added.
Figure 12B:
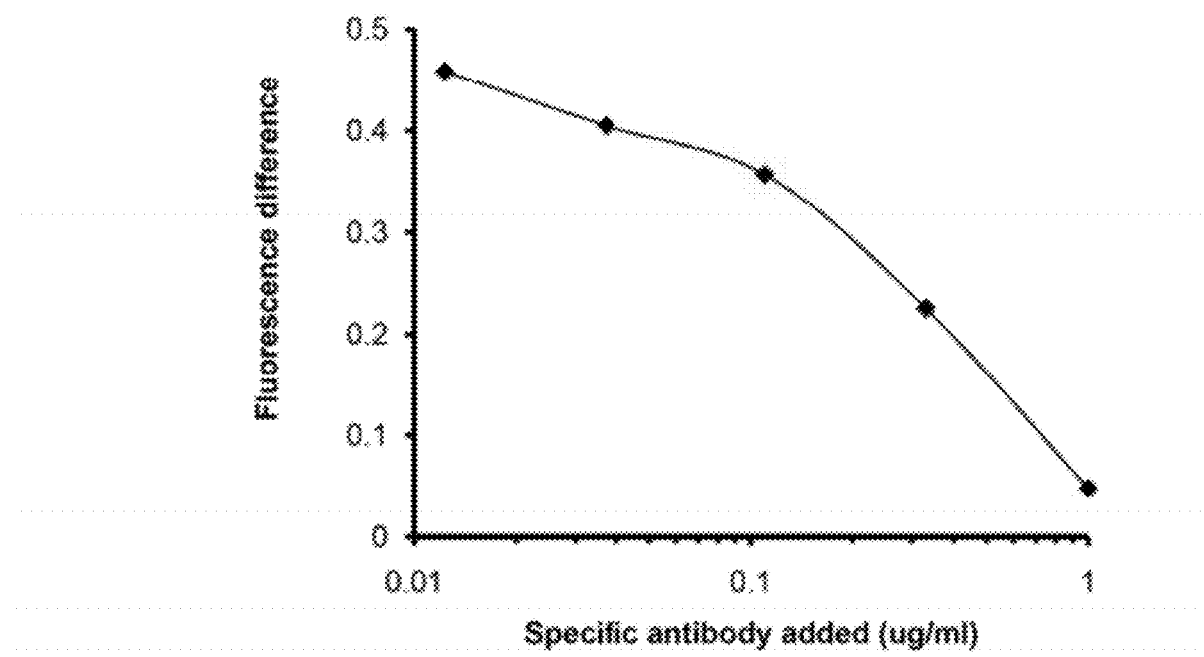
FIG. 12B is a graph showing a concentration-response curve for the assay of FIG. 11A.

As shown in FIG. 12A, the addition of the antibody increased the quenching of the fluorescent microparticles. FIG. 12B show that the quenching was concentration dependent to about 0.03 µg/ml of anti-human serum albumin added. The concentration dependence was identical in the presence and absence of rabbit serum (data not shown).

Example 6

Substrate Generation with an Immobilized Enzyme and a Precursor Substrate

In the presence of, glucose, the enzyme glucose oxidase (EC 1.1.3.4) produces the products D-gluconic acid and hydrogen peroxide. The glucose is therefore a precursor substrate for the generation of hydrogen peroxide. The hydrogen peroxide formed by immobilized glucose oxidase is then used as a co-substrate by the HRP, the optical signal amplifier, in the optical signal generating reaction.

Figure 13A:
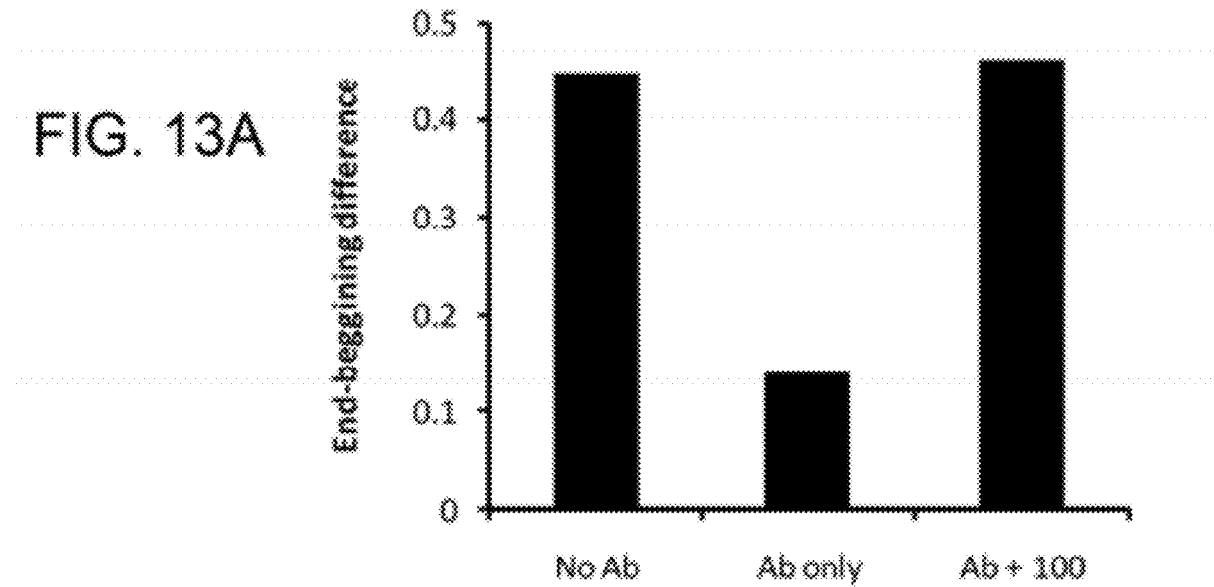
FIG. 13A is a graph of showing the florescence difference signal generated in a human serum albumin assay where immobilized glucose oxidase produces hydrogen peroxide.

Lucifer Yellow, 2-chloro-phenylene-1,4-diamine, glucose oxidase, and albumin were sequentially immobilized on the microparticles as described above. The glucose oxidase was immobilized at a concentration of 0.1 mg/ml of microparticles for one hour in the presence of 20 mM sodium cyanoborohydride in 50 mM sodium acetate buffer, pH 6.0. The assay was run as in the albumin competitive immunoassay example, except that 4-methoxy phenol was used as a coupler and instead of using barium peroxide as the peroxide source, glucose was added to a concentration of 10 mM as a substrate for glucose oxidase to generate hydrogen peroxide. As can be seen in FIG. 13A the addition of the mouse anti-albumin-HRP conjugate caused a marked decrease in the fluorescence difference measurement which was completely reversed by the addition of 100 µg/ml of free albumin.

Example 7

Substrate Generation with an Immobilized Enzyme and a Blocked Substrate

Phosphate is a commonly used blocking group on substrates. Phosphatase enzymes readily cleave the ester bond, generating free phosphate and a compound with a hydroxyl group where the phosphate was attached. This example uses calf intestinal alkaline phosphatase (EC 3.1.3.1), a hydrolase enzyme that requires a divalent cation such as magnesium as a cofactor, and 1-naphthol phosphate as the blocked substrate.

Lucifer Yellow (fluorochrome), albumin (a first ligand), and alkaline phosphatase were sequentially immobilized on the microparticles as described above. The alkaline phosphatase was immobilized at a concentration of 1 mg/ml of microparticles for one hour in the presence of 20 mM sodium cyanoborohydride in 10 mM magnesium chloride, 50 mM sodium acetate buffer, pH 6.0. The assay was run as in the albumin competitive immunoassay example, except that instead of using 1-naphthol as a dimerizing or polymerizing substrate, the blocked substrate 1-naphthol phosphate was used and the buffer contained 1 mM $MgCl_2$ to keep the alkaline phosphatase active.

Figure 13B:
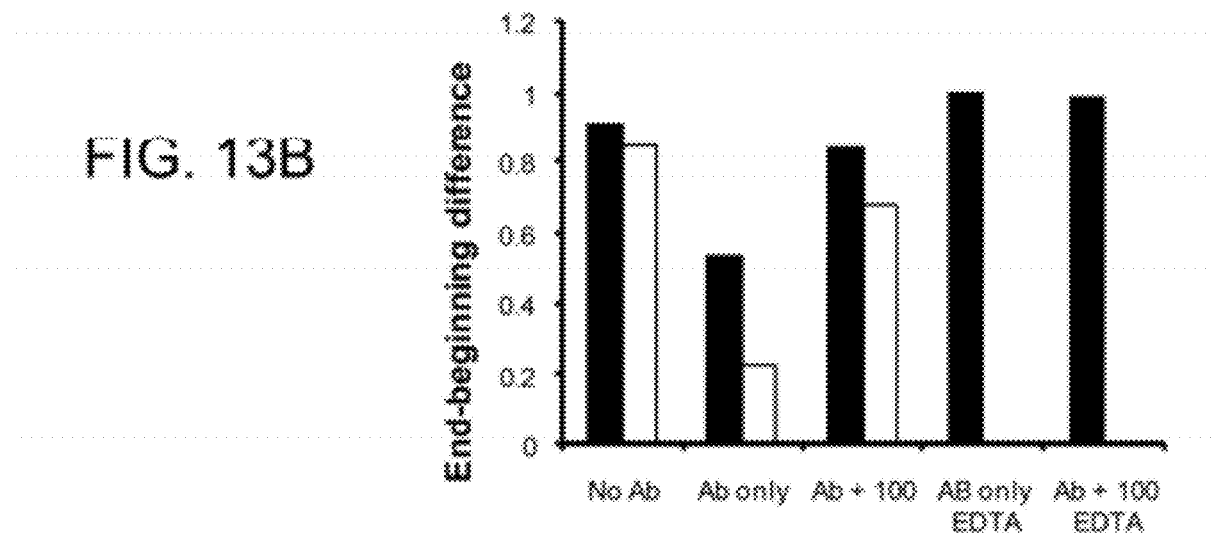
FIG. 13B is a graph of the fluorescence difference signal generated in an assay for human serum albumin (analyte) where immobilized alkaline phosphatase (a substrate-generating enzyme) is used to remove a blocking group from a substrate. The filled bars indicate assays performed using the blocked substrate 1-naphthyl phosphate and the open bars indicate assays performed using the unblocked substrate 1-naphthol.

As can be seen in FIG. 13B the addition of the mouse anti-albumin HRP conjugate caused a marked decrease in the fluorescence difference measurement which was reversed by the addition of 100 µg/ml of albumin. To show that the optical signal generated was dependent on the alkaline phosphatase, the $MgCl_2$ was removed from the buffer and 10 mM EDTA, a divalent cation chelator, was added. In this condition, the fluorescence signal detected was not different from that observed in the absence of the HRP-antibody conjugate. Active alkaline phosphatase was therefore necessary for the optical signal generation reaction to take place. The open bars in FIG. 13B show assays performed unblocked 1-naphthol.

When comparing the assays with the blocked and unblocked substrates, there was 3.9-fold more residual quenching in the presence of 100 μg/ml albumin. The working signal, as measured by the difference in fluorescence between the absence and presence of 100 mg/ml albumin, was only 37% less in the blocked substrate assays. The blocked substrate assay therefore has a 2,4-fold better signal to noise ratio than the unblocked substrate assay.

Alternatively, a functionalized microparticle without immobilized fluorochrome may be used. In this case, the functionalized microparticle comprises albumin (the first ligand) and alkaline phosphatase (an enzyme for generating an intermediate reagent). The optical signal of the final colored product is the absorbance of the light at a wavelength of 620 nm.

Example 8

Assay Involving a Blocked Coupler

This assay requires:
(a) providing a functionalized microparticle comprising immobilized functional components as follows: a first ligand; a color forming substrate; and an enzyme for generating an intermediate reagent; and
(b) providing a buffer solution and functional components as follows: an optical signal amplifier attached to a second ligand; a co-substrate; a blocked coupler.

As a demonstration for assaying the analyte insulin, a competitive assay involving a blocked coupler may be performed as follows. The functionalized microparticle has immobilized insulin C peptide (a first ligand); 2-chloro-phenylene-1,4-diamine (a color forming substrate); and alkaline phosphatase (an enzyme for generating an intermediate reagent). The buffer solution may be added HRP-anti-insulin C-peptide antibody (an optical signal amplifier attached to a second ligand); hydrogen peroxide (a co-substrate); 1-phospho-2,4-dichloro-1-naphthol (a blocked coupler).

After admixing a sample containing the analyte insulin C peptide (which has no intrinsic optical contrast) with the aforementioned buffer solution and the functionalized microparticles, the following reactions occur and an optical signal is generated in the microparticle.

In this case, HRP-anti-insulin C peptide antibody (an optical signal amplifier attached to a second ligand) binds to the immobilized albumin (a first ligand) and/or the insulin C peptide (analyte) in the sample.

The immobilized alkaline phosphatase (an enzyme for generating an intermediate reagent) dephosphorylates the 1-phospho-2,4-dichloro-1-naphthol (a blocked coupler) and forms 2,4-dichloro-1-naphthol (unblocked coupler).

The HRP in the HRP-anti-insulin C peptide antibody (an optical signal amplifier attached to a second ligand) activates the immobilized 2-chloro-2-chloro-phenylene-1,4-diamine (a color forming substrate) to form an intermediate, which then couples with the 2,4-dichloro-1-naphthol (unblocked coupler) and forms a colored product. The optical signal of the colored product is then measured by its absorbance of the light at 620 nm.

Example 9

Assay Involving a Coupler

This assay requires:
(a) providing a functionalized microparticle comprising immobilized functional components as follows: a first ligand; and a color forming substrate; and
(b) providing a buffer solution and functional components as follows: an optical signal amplifier attached to a second ligand; a co-substrate; and a coupler.

As a demonstration for assaying the analyte Prostate-Specific Antigen (PSA), a competitive assay involving a coupler may be performed as follows. The functionalized microparticle has immobilized anti-PSA antibody (a first ligand); and 2-chloro-phenylene-1,4-diamine (a color forming substrate). The buffer solution may be added HRP-PSA (an optical signal amplifier attached to a second ligand); hydrogen peroxide (a co-substrate); 4-methoxyphenol (a coupler).

After admixing a sample containing the analyte PSA (which has no intrinsic optical contrast) with the aforementioned buffer solution and the functionalized microparticles, the following reactions occur and an optical signal is generated in the microparticles.

In this case, the PSA (analyte) in the sample and the HRP-PSA (an optical signal amplifier attached to a second ligand) in the buffer solution competes for the binding to the immobilized anti-albumin antibody (a first ligand) on the functionalized microparticles.

Then the HRP in the HRP-PSA (an optical signal amplifier attached to a second ligand) activates the immobilized 2-chloro-phenylene-1,4-diamine (a color forming substrate) in the presence of the hydrogen peroxide (a co-substrate) to form an intermediate, which in turn couples with 4-methoxyphenol (a coupler) and form a colored product. The optical signal of the colored product is then measured by its absorbance of the light at 620 nm.

Example 10

Assay with One Functional Component in a Buffer Solution

This assay requires:
(a) providing a functionalized microparticle comprising immobilized functional components as follows: a first ligand; and a color forming substrate; and
(b) providing a buffer solution and one functional component, i.e., an optical signal amplifier attached to a second ligand.

As a demonstration for assaying the analyte Alpha Fetoprotein (AP), an assay with one functional component in a buffer solution may be performed as follows. The functionalized microparticle has immobilized anti-AP antibody (a first ligand); and a substrate for β-galactosidase (a color forming substrate). The buffer solution may be added β-galactosidase-anti-AP antibody (an optical signal amplifier attached to a second ligand). The immobilized substrate for β-galactosidase may be 5-bromo-4-chloro-3-indolyl-beta-D-galactopyranoside, which can be attached to the microparticle at the end of the agarose chains.

After admixing a sample containing the analyte AP (which has no intrinsic optical contrast) with the aforementioned buffer solution and the functionalized microparticles, the following reactions occur and an optical signal is generated in the microparticles.

In this case, the AP (analyte) in the sample binds to the immobilized anti-AP antibody on the microparticle as well as the anti-AP antibody on the β-galactosidase-anti-AP antibody in the buffer solution, forming a sandwich. The β-galactosidase-anti-AP antibody is now indirectly attached to the functionalized microparticle through the analyte in the sample and the immobilized anti-AP antibody (first ligand). The β-galactosidase on the β-galactosidase-anti-AP antibody can catalyze the immobilized substrate for β-galactosidase and forms a colored product in the microparticles. The immobilized substrate here is cleaved by β-galactosidase yielding 5-bromo-4-chloro-3-hydroxyindole, which is then oxidized into 5,5'-dibromo-4,4'-dichloro-indigo, an insoluble blue product.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of performing a two-phase optical assay of one or more than one analyte without intrinsic optical contrast in a sample, comprising:
   (a) providing functionalized microparticles, the functionalized microparticles each comprising immobilized two or more than two functional components,
      wherein the two or more than two functional components are selected from the group consisting of:
         (i) a first ligand;
         (ii) a color forming substrate;
         (iii) an enzyme for generating an intermediate reagent; and
         (iv) a fluorochrome,
      and wherein at least one of the two or more than two functional components is the first ligand;
   (b) providing a buffer solution and one or more than one functional component, the one or more than one functional component being the same or different from the two or more than two functional components immobilized to the microparticle in step (a) and being selected from the group consisting of:
      (i) an optical signal amplifier attached to a second ligand;
      (ii) a color forming substrate;
      (iii) a co-substrate;
      (iv) a blocked substrate or a blocked coupler;
      (v) a precursor substrate;
      (vi) a coupler;
      (vii) an enzyme for generating an intermediate reagent; and
      (viii) a fluorochrome;
   (c) admixing a sample comprising one or more than one analyte without intrinsic optical contrast with the buffer solution, the one or more than one functional component, and the functionalized microparticles in a container to form a two-phase suspension with the functionalized microparticles suspended in the buffer solution;
   (d) allowing the one or more than one analyte to bind the first ligand and/or the second ligand attached to the optical signal amplifier and to develop an optical signal in the microparticles;
   (e) measuring the optical signal of the two-phase suspension having the functionalized microparticles suspended in the buffer to obtain a first measurement;
   (f) allowing the functionalized microparticles to settle to the bottom of the container to obtain a microparticle-rich phase at the bottom of the container and a microparticle-free phase above the microparticle-rich phase;
   (g) measuring the optical signal of the microparticle-rich phase to obtain a second measurement; and
   (h) calculating an algorithmic relationship between the first and second measurements and comparing the calculated algorithmic relationship to a standard curve to determine the concentration of the one or more than one analyte.

2. The method of claim 1, wherein:
   the step (d) causes the one or more than one functional component in the buffer solution to indirectly attach to the functionalized microparticles through the analyte that is bound to the immobilized first ligand on the functionalized microparticles; or
   the step (d) causes the analyte to compete for binding to the first or second ligand, preventing the second ligand from binding to the immobilized first ligand on the functionalized microparticles.

3. The method of claim 2, wherein the optical signal amplifier attached to the second ligand is an enzyme.

4. The method of claim 3, wherein the enzyme is a peroxidase.

5. The method of claim 1, wherein the functionalized microparticles in step (a) each comprise the immobilized first ligand and the immobilized fluorochrome.

6. The method of claim 1, wherein the functionalized microparticles in step (a) each comprise the immobilized first ligand and the immobilized color forming substrate.

7. The method of claim 6, wherein the functionalized microparticles in step (a) each further comprise the immobilized fluorochrome.

8. The method of claim 6, wherein the color forming substrate comprises an aromatic compound having two or more than two amine functional groups, one of the two or more than two amine functional groups being attached to the microparticles to form the functionalized microparticles.

9. The method of claim 8, wherein the aromatic compound is selected from the group consisting of 2-chloro-phenylene-1,4-diamine, diaminobenzidine, ortho-dianisidine, 1,4-diamino-naphthalene and derivatives thereof.

10. The method of claim 1, wherein the functionalized microparticles each comprise the immobilized first ligand, the immobilized color forming substrate, the immobilized fluorochrome, and the immobilized enzyme for generating the intermediate reagent.

11. The method of claim 1, wherein the admixing step causes the color forming substrate to dimerize or polymerize and form a colored product.

12. The method of claim 11, wherein the functionalized microparticles in step (a) each further comprise the immobilized fluorochrome.

13. The method of claim 11, wherein the immobilized enzyme for generating the intermediate reagent comprises an oxidase other than peroxidase, and produces hydrogen peroxide after the admixing step (c).

14. The method of claim 1, wherein the step (b) provides more than one functional component, which comprises:
 (i) the optical signal amplifier attached to the second ligand, wherein the optical signal amplifier comprises an enzyme;
 (ii) the co-substrate; and
 (iii) the blocked substrate.

15. The method of claim 14, wherein the immobilized enzyme for generating the intermediate reagent comprises a hydrolase.

16. The method of claim 14, wherein the functionalized microparticles in step (a) each comprise:
 (i) the first ligand;
 (ii) optionally the color forming substrate;
 (iii) the enzyme for generating an intermediate reagent; and
 (iv) optionally the fluorochrome.

17. The method of claim 1, wherein step (h) calculates a difference between the first and second measurements.

18. The method of claim 1, wherein step (h) calculates a ratio of the first and second measurements.

19. The method of claim 1, wherein the container in step (c) is closable with a cover, or is open without a cover and the container has a point at the bottom or has a V-shaped bottom.

20. The method of claim 19, wherein the cover has multiple compartments for segregating and storing the one or more than one functional component.

* * * * *